(12) United States Patent
Dubois et al.

(10) Patent No.: US 8,394,820 B2
(45) Date of Patent: Mar. 12, 2013

(54) N-AZABICYCLIC CARBOXAMIDE DERIVATIVES, PREPARATION THEREOF AND THERAPEUTIC USE THEREOF

(75) Inventors: Laurent Dubois, Paris (FR); Yannick Evanno, Paris (FR); André Malanda, Paris (FR); Odile LeClerc, Paris (FR)

(73) Assignee: Sanofi, Paris (FR)

( * ) Notice: Subject to any disclaimer, the term of this patent is extended or adjusted under 35 U.S.C. 154(b) by 196 days.

(21) Appl. No.: 12/840,664

(22) Filed: Jul. 21, 2010

(65) Prior Publication Data

US 2011/0009444 A1 Jan. 13, 2011

Related U.S. Application Data

(63) Continuation of application No. PCT/FR2009/000053, filed on Jan. 20, 2009.

(30) Foreign Application Priority Data

Jan. 22, 2008 (FR) ...................................... 08 00310

(51) Int. Cl.
*A61K 31/437* (2006.01)
*C07D 471/00* (2006.01)
(52) U.S. Cl. ......... 514/300; 546/112; 546/113; 514/299
(58) Field of Classification Search .................. 546/112, 546/113; 514/299, 300
See application file for complete search history.

(56) References Cited

U.S. PATENT DOCUMENTS

| | | | | |
|---|---|---|---|---|
| 7,407,950 B2 * | 8/2008 | Dubois et al. | ............ | 514/211.09 |
| 7,763,636 B2 * | 7/2010 | Dubois et al. | ................. | 514/300 |
| 7,786,104 B2 * | 8/2010 | DuBois et al. | ............. | 514/210.2 |
| 7,868,024 B2 * | 1/2011 | Dubois et al. | ................. | 514/339 |
| 8,044,066 B2 * | 10/2011 | Dubois et al. | ................. | 514/300 |
| 8,143,248 B2 * | 3/2012 | Dubois et al. | ................. | 514/230.2 |
| 8,153,650 B2 * | 4/2012 | Dubois et al. | ................. | 514/299 |

FOREIGN PATENT DOCUMENTS

WO WO2007/088277 A1 8/2007

OTHER PUBLICATIONS

International Search Report dated Jul. 16, 2009 issued in PCT/FR2009/000053.

* cited by examiner

*Primary Examiner* — Golam M M Shameem
(74) *Attorney, Agent, or Firm* — Scully, Scott, Murphy & Presser, P.C.

(57) ABSTRACT

This disclosure relates to compounds of formula (I):

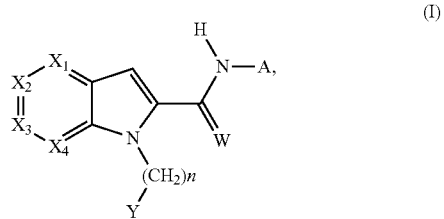

wherein $X_1$, $X_2$, $X_3$, $X_4$, n, Y, W, and A are as defined in the disclosure, or a salt thereof, or a hydrate or solvate thereof, and to processes for the preparation of these compounds and the therapeutic use thereof.

17 Claims, No Drawings

N-AZABICYCLIC CARBOXAMIDE DERIVATIVES, PREPARATION THEREOF AND THERAPEUTIC USE THEREOF

Documents WO2006/024776, WO2006/072736, WO2007/010144 and WO2007/010138 describe bicyclic carboxamide derivatives with in vitro and in vivo antagonist or agonist activity on receptors of TRPV1 (or VR1) type.

There is still a need to find novel ligands for receptors of TRPV 1 type, which are improved in terms of functional activity, metabolic profile and/or safety profile.

The present invention satisfies this need by providing azabicyclic carboxamide derivatives that have in vitro and in vivo antagonist or agonist activity on receptors of TRPV1 (or VR1) type.

A first subject of the invention concerns the compounds corresponding to the general formula (I) hereinbelow.

Another subject of the invention concerns processes for preparing the compounds of general formula (I).

Another subject of the invention concerns the use of the compounds of general formula (I) especially in medicaments or in pharmaceutical compositions.

The compounds of the invention correspond to the general formula (I):

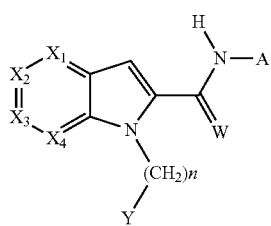

in which:

$X_1$, $X_2$, $X_3$ and $X_4$ represent, independently of each other, a nitrogen atom or a group C—$R_1$;

it being understood that when one from among $X_1$, $X_2$, $X_3$ and $X_4$ represents a nitrogen atom, the others correspond to a group C—$R_1$;

W represents an oxygen or sulfur atom;

n is equal to 0, 1, 2 or 3;

Y represents an aryl or a heteroaryl optionally substituted with one or more groups chosen from a halogen atom and a group $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl, hydroxyl, $C_1$-$C_6$-alkoxy, $C_3$-$C_7$-cycloalkyloxy, $C_3$-$C_7$-cycloalkyl-$C_1$-$C_6$-alkylene-O—, $C_1$-$C_6$-fluoroalkoxy, cyano, C(O)$NR_3R_4$, nitro, $NR_3R_4$, $C_1$-$C_6$-thioalkyl, thiol, —S(O)—$C_1$-$C_6$-alkyl, —S(O)$_2$-$C_6$-alkyl, $SO_2NR_3R_4$, $NR_5C(O)R_6$, $NR_5SO_2R_7$, C(O)$NR_3R_4$, OC(O)$NR_3R_4$, —Si—($C_1$-$C_6$-alkyl)$_3$, —SF$_5$, aryl-$C_1$-$C_5$-alkylene or aryl, heteroaryl-$C_1$-$C_5$-alkylene or heteroaryl; the groups $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl, $C_1$-$C_6$-alkoxy, $C_3$-$C_7$-cycloalkyloxy and $C_3$-$C_7$-cycloalkyl-$C_1$-$C_6$-alkylene-O— possibly being substituted with a hydroxyl, $C_1$-$C_6$-alkoxy or $NR_3R_4$ group; the aryl and heteroaryl groups being optionally substituted with one or more substituents $R_8$, which may be identical to or different from each other;

A represents a bicyclic heteroaryl of formula:

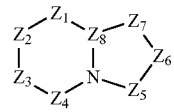

in which $Z_1$, $Z_2$, $Z_3$ and $Z_4$ represent, independently of each other, a carbon atom, a nitrogen atom or a group C—$R_{2a}$;

$Z_5$, $Z_6$ and $Z_7$ represent, independently of each other, a nitrogen atom or a group C—$R_{2b}$;

$Z_8$ represents a carbon atom;

three, at most, from among $Z_1$, $Z_2$, $Z_3$, $Z_4$, $Z_5$, $Z_6$ and $Z_7$ represent a nitrogen atom;

one from among $Z_1$, $Z_2$, $Z_3$ and $Z_4$, corresponding to a carbon atom, being bonded to the nitrogen atom of the amide or thioamide of formula (I);

$R_1$ is chosen from a hydrogen atom, a halogen atom, $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl, aryloxy-$C_1$-$C_6$-alkyl, heteroaryloxy-$C_1$-$C_6$-alkyl, aryl-$C_1$-$C_3$-alkylenoxy-$C_1$-$C_6$-alkyl, heteroaryl-$C_1$-$C_3$-alkylenoxy-$C_1$-$C_6$-alkyl, arylthio-$C_1$-$C_6$-alkyl, heteroarylthio-$C_1$-$C_6$-alkyl, aryl-$C_1$-$C_3$-alkylenethio-$C_1$-$C_6$-alkyl, heteroaryl-$C_1$-$C_3$-alkylenethio-$C_1$-$C_6$-alkyl, $C_1$-$C_6$-alkoxy, $C_3$-$C_7$-cycloalkyloxy, $C_3$-$C_7$-cycloalkyl-$C_1$-$C_3$-alkylenoxy, $C_1$-$C_6$-fluoroalkoxy, cyano, C(O)$NR_3R_4$, nitro, $NR_3R_4$, $C_1$-$C_6$-thioalkyl, $C_3$-$C_7$-cycloalkylthio, $C_3$-$C_7$-cycloalkyl-$C_1$-$C_3$-alkylenethio, —S(O)—$C_1$-$C_6$-alkyl, —S(O)—$C_3$-$C_7$-cycloalkyl, —S(O)—$C_1$-$C_3$-alkylene-$C_3$-$C_7$-cycloalkyl, $C_1$-$C_6$-alkyl-S(O)$_2$—, $C_1$-$C_6$-fluoroalkyl-S(O)$_2$—, $C_3$-$C_7$-cycloalkyl-S(O)$_2$—, $C_3$-$C_7$-cycloalkyl-$C_1$-$C_3$-alkylene-S(O)$_2$—, $SO_2NR_3R_4$, ($C_1$-$C_6$-alkyl)$_3$-Si—, —SF$_5$, $NR_5C(O)R_6$, $NR_5SO_2R_7$, C(O)$NR_3R_4$, OC(O)$NR_3R_4$, aryl, heteroaryl, aryl-$C_1$-$C_5$-alkylene, heteroaryl-$C_1$-$C_5$-alkylene, aryloxy, arylthio, heteroaryloxy or heteroarylthio; the heteroaryl or aryl groups being optionally substituted with one or more substituents $R_8$, which may be identical to or different from each other;

$R_{2a}$ represents a hydrogen atom, a halogen atom or a group $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl, $C_1$-$C_6$-alkoxy, $C_3$-$C_7$-cycloalkyloxy, $C_3$-$C_7$-cycloalkyl-$C_1$-$C_3$-alkylene-O—, hydroxyl, thiol or $C_1$-$C_6$-fluoroalkoxy;

$R_{2b}$ represents a hydrogen atom, a halogen atom or a group $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl, $C_1$-$C_6$-alkoxy, hydroxyl, thiol, oxo, thio, $C_3$-$C_7$-cycloalkyloxy, $C_1$-$C_6$-fluoroalkoxy, $C_3$-$C_7$-cycloalkyl-$C_1$-$C_3$-alkylenoxy, $C_1$-$C_6$-alkoxy-$C_1$-$C_3$-alkylene, $C_3$-$C_7$-cycloalkyloxy-$C_1$-$C_3$-alkylene, $C_3$-$C_7$-cycloalkyl-$C_1$-$C_3$-alkylenoxy-$C_1$-$C_3$-alkylene, $C_1$-$C_6$-alkyl-C(O)—O—$C_1$-$C_3$-alkylene, $C_1$-$C_6$-alkyl-C(O)—O—, $C_3$-$C_7$-cycloalkyl-C(O)—O—$C_1$-$C_3$-alkylene, $C_3$-$C_7$-cycloalkyl-C(O)—O—, $C_1$-$C_6$-fluoroalkyl-C(O)—O—$C_1$-$C_3$-alkylene, $C_1$-$C_6$-fluoroalkyl-C(O)—O—, C(O)$NR_3R_4$, C(O)O—$C_1$-$C_6$-alkyl, cyano, CHO, $CO_2H$, —C(O)—$C_1$-$C_6$-alkyl, —C(O)—$C_3$-$C_7$-cycloalkyl, phenyl or thienyl; the groups $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl, $C_1$-$C_6$-alkoxy, $C_3$-$C_7$-cycloalkyloxy, $C_1$-$C_6$-fluoroalkoxy, $C_3$-$C_7$-cycloalkyl-$C_1$-$C_3$-alkylenoxy, $C_1$-$C_6$-alkoxy-$C_1$-$C_3$-alkylene, $C_3$-$C_7$-cycloalkyloxy-$C_1$-$C_3$-alkylene and $C_3$-$C_7$-cycloalkyl-$C_1$-$C_3$-alkylenoxy-$C_1$-$C_3$-alkylene possibly being substituted with a hydroxyl, $C_1$-$C_6$-alkoxy or $NR_3R_4$ group;

$R_3$ and $R_4$ represent, independently of each other, a hydrogen atom or a group $C_1$-$C_6$-alkyl, $C_3$-$C_7$-cycloalkyl, $C_3$-$C_7$-cycloalkyl-$C_1$-$C_3$-alkylene, aryl-$C_1$-$C_5$-alkylene or aryl, or $R_3$ and $R_4$ together form, with the nitrogen atom that bears them, an azetidine, pyrrolidine, piperidine, azepine, morpholine, thiomorpholine, piperazine or homopiperazine group; the group $NR_3R_4$ being optionally substituted with a group $C_1$-$C_6$-alkyl, $C_3$-$C_7$-cycloalkyl, $C_3$-$C_7$-cycloalkyl-$C_1$-$C_3$-alkylene, aryl-$C_1$-$C_6$-alkylene, aryl, heteroaryl, aryl-S(O)$_2$—, $C_1$-$C_6$-alkyl-S(O)$_2$—, $C_1$-$C_6$-fluoroalkyl-S(O)$_2$, $C_3$-$C_7$-cycloalkyl-S(O)$_2$—, $C_3$-$C_7$-cycloalkyl-$C_1$-$C_3$-alkylene-S(O)$_2$—, aryl-C(O)—, $C_1$-$C_6$-alkyl-C(O)—, $C_3$-$C_7$-cycloalkyl-C(O)—, $C_3$-$C_7$-cycloalkyl-$C_1$-$C_3$-alkylene-C(O)—, $C_1$-$C_6$-fluoroalkyl-C(O)—, hydroxyl, $C_1$-$C_6$-alkyloxy, $C_3$-$C_7$-cycloalkyloxy, $C_3$-$C_7$-cycloalkyl-$C_1$-$C_3$-alkylenoxy, $C_1$-$C_6$-fluoroalkyl, aryloxy-$C_1$-$C_6$-alkylene, aryloxy, heteroaryloxy-$C_1$-$C_6$-alkylene or heteroaryloxy;

$R_5$ and $R_6$ represent, independently of each other, a hydrogen atom or a group $C_1$-$C_6$-alkyl, $C_3$-$C_7$-cycloalkyl, $C_3$-$C_7$-cycloalkyl-$C_1$-$C_3$-alkylene, aryl-$C_1$-$C_6$-alkylene or aryl; the aryl group being optionally substituted with one or more substituents chosen from a halogen atom and a group $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl, $C_1$-$C_6$-alkoxy, $C_3$-$C_7$-cycloalkyloxy, $C_3$-$C_7$-cycloalkyl-$C_1$-$C_3$-alkylenoxy, $C_1$-$C_6$-fluoroalkoxy, nitro or cyano;

or $R_5$ and $R_6$ together form a 4- to 7-membered lactam comprising the nitrogen atom and the C(O) group that bear them;

$R_7$ represents a group $C_1$-$C_6$-alkyl, $C_3$-$C_7$-cycloalkyl, $C_3$-$C_7$-cycloalkyl-$C_1$-$C_3$-akylene, aryl-$C_1$-$C_6$-alkylene or aryl; the aryl group being optionally substituted with one or more substituents chosen from a halogen atom and a group $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl, $C_1$-$C_6$-alkoxy, $C_3$-$C_7$-cycloalkyloxy, $C_3$-$C_7$-cycloalkyl-$C_1$-$C_3$-alkylenoxy, $C_1$-$C_6$-fluoroalkoxy, nitro or cyano;

or $R_5$ and $R_7$ together form a 4- to 7-membered sultam comprising the nitrogen atom and the S(O)$_2$ group that bear them;

$R_8$ represents a halogen atom or a group $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl, $C_1$-$C_6$-alkoxy, $C_3$-$C_7$-cycloalkyloxy, $C_3$-$C_7$-cycloalkyl-$C_1$-$C_3$-alkylenoxy, $C_1$-$C_6$-fluoroalkoxy, nitro, cyano, $NR_3R_4$, —C(O)—$C_1$-$C_6$-alkyl or —C(O)—$C_3$-$C_7$-cycloalkyl; the groups $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl, $C_1$-$C_6$-alkoxy, $C_3$-$C_7$-cycloalkyloxy and $C_3$-$C_7$-cycloalkyl-$C_1$-$C_3$-alkylenoxy possibly being substituted with a group OH, $C_1$-$C_6$-alkoxy or $NR_3R_4$.

In the compounds of general formula (I):
the sulfur atom(s) may be in oxidized form (S(O) or S(O)$_2$);
the nitrogen atom(s) may optionally be in oxidized form (N-oxide).

The compounds of formula (I) may comprise one or more asymmetric carbon atoms. They may thus exist in the form of enantiomers or diastereoisomers. These enantiomers and diastereoisomers, and also mixtures thereof, including racemic mixtures, form part of the invention.

The compounds of formula (I) may exist in the form of bases or of acid-addition salts. Such addition salts form part of the invention.

These solvents may be prepared with pharmaceutically acceptable acids, but the salts of other acids that are useful, for example, for purifying or isolating the compounds of formula (I) also form part of the invention.

The compounds of formula (I) may also exist in the form of hydrates or solvates, i.e. in the form of associations or combinations with one or more water molecules or with a solvent. Such hydrates and solvates also form part of the invention.

In the context of the present invention, the following definitions apply:
a halogen atom: a fluorine, a chlorine, a bromine or an iodine;
$C_t$-$C_z$: a carbon-based chain possibly containing from t to z carbon atoms in which t and z may take values from 1 to 7; for example, $C_1$-$C_3$ is a carbon-based chain possibly containing from 1 to 3 carbon atoms;
an alkyl: a linear or branched saturated aliphatic group. Examples that may be mentioned include methyl, ethyl, propyl, isopropyl, butyl, isobutyl, tert-butyl, pentyl, etc.;
an alkylene: a linear or branched saturated divalent alkyl group, for example a group $C_{1-3}$-alkylene represents a linear or branched divalent carbon-based chain of 1 to 3 carbon atoms, more particularly a methylene, ethylene, 1-methylethylene or propylene;
a cycloalkyl: a saturated or partially unsaturated cyclic alkyl group. Examples that may be mentioned include the groups cyclopropyl, cyclobutyl, cyclopentyl, cyclohexyl, etc.;
a cycloalkyloxy: a radical —O-cycloalkyl in which the cycloalkyl group is as defined previously;
a fluoroalkyl: an alkyl group, one or more hydrogen atoms of which have been replaced with a fluorine atom;
an alkoxy: a radical —O-alkyl in which the alkyl group is as defined previously;
a fluoroalkoxy: an alkoxy group, one or more hydrogen atoms of which have been replaced with a fluorine atom;
a thioalkyl or alkylthio: a radical —S-alkyl in which the alkyl group is as defined previously;
an aryl: a monocyclic or bicyclic aromatic group containing between 6 and 10 carbon atoms. Examples of aryl groups that may be mentioned include phenyl and naphthyl groups;
a heteroaryl: a monocyclic or bicyclic aromatic group 5- to 12-membered containing from 1 to 5 heteroatoms chosen from O, S and N.

Examples of monocyclic heteroaryls that may be mentioned include imidazolyl, pyrazolyl, thiazolyl, oxazolyl, isothiazolyl, isoxazolyl, furyl, thiophenyl, oxadiazolyl, thiadiazolyl, triazolyl, tetrazolyl, pyridyl, pyrazinyl, pyrimidinyl, pyridazinyl and triazinyl.

Examples of bicyclic heteroaryls that may be mentioned include indolyl, isoindolyl, benzofuryl, benzothiophenyl, benzoxazolyl, benzimidazolyl, indazolyl, benzothiazolyl, isobenzofuryl, isobenzothiazolyl, pyrrolo[2,3-c]pyridyl, pyrrolo[2,3-b]pyridyl, pyrrolo[3.2-b]pyridyl, pyrrolo[3.2-c]pyridyl, pyrrolo[1,2-a]pyridyl, quinolyl, isoquinolyl, cinnolinyl, quinazolinyl, quinoxalinyl, pyrrolo[1,2-a]imidazolyl, imidazo[1,2-a]pyridyl, imidazo[1,5-a]pyridyl, imidazo[1,2-b]pyridazinyl, imidazo[1,2-c]pyrimidinyl, imidazo[1,2-a]pyrimidinyl, imidazo[1,5-a]pyrimidinyl, imidazo[1,5-c]pyrimidinyl, imidazo[1,2-a]pyrazinyl, imidazo[1,5-a]pyrazinyl, imidazo[1,5-b]pyridazinyl, imidazo[4.5-b]pyrazinyl, imidazo[4.5-b]pyridyl, imidazo[4.5-c]pyridyl, pyrazolo[1,5-a]pyridyl, pyrazolo[1,5-a]pyrimidinyl, pyrazolo[1,5-c]pyrimidinyl, pyrazolo[1,5-a]pyrazinyl, pyrazolo[1,5-b]pyridazinyl, indolizinyl, pyrrolo[1,2-b]pyridazinyl, pyrrolo[1,2-c]pyrimidinyl, pyrrolo[1,2-a]pyrazinyl, pyrrolo[1,2-a]pyrimidinyl, [1,2,4]triazolo[4.3-a]pyridyl, [1,2,4]triazolo[2,3-a]pyridyl, [1,2,4]triazolo[1,5-a]pyridyl, [1.2.3]triazolo[1,5-a]pyridyl, [1,2,4]triazolo[1,5-b]pyridazinyl, triazolo[1,2-a]pyrimidinyl, triazolo[1,2-c]pyrimidinyl, triazolo[1,2-a]

pyrazinyl, triazolo[1,2-b]pyridazinyl, [1,2,4]triazolo[1,5-b]pyridazinyl, [1,2,4]triazolo[1,5-c]pyrimidinyl, [1,2,4]triazolo[1,2-a]pyrazinyl, [1,2,4]triazolo[1,5-a]pyrimidinyl, [1.2.3]triazolo[1,5-b]pyridazinyl, [1.2.3]triazolo[1,5-c]pyrimidinyl, [1.2.3]triazolo[1,2-a]pyrazinyl, [1.2.3]triazolo[1,5-a]pyrimidinyl, imidazo[1,2-d][1,2,4]triazinyl, imidazo[2.1-f][1,2,4]triazinyl, imidazo[1,2-b][1,2,4]triazinyl, imidazo[1,2-a][1.3.5]triazinyl, imidazo[2.1-c][1,2,4]triazinyl, imidazo[5.1-c][1,2,4]triazinyl, imidazo[1,5-a][1.3.5]triazinyl, imidazo[1,5-b][1,2,4]triazinyl, imidazo[5.1-f][1,2,4]triazinyl, imidazo[1,5-d][1,2,4]triazinyl, imidazo[1,5-c][1.2.3]triazinyl, pyrazolo[5.1-c][1,2,4]triazinyl, pyrazolo[1,5-a][1.3.5]triazinyl, pyrazolo[1,5-b][1,2,4]triazinyl, pyrazolo[5.1-f][1,2,4]triazinyl, pyrazolo[1,5-d][1,2,4]triazinyl and pyrazolo[1,5-c][1.2.3]triazinyl groups;

"oxo" means "=O";

"thio" means "=S".

Among the compounds of general formula (I) that are subjects of the invention, a first subgroup of compounds is constituted by the compounds for which $X_1$, $X_2$, $X_3$ and $X_4$ represent, independently of each other, a group $C$—$R_1$;

$R_1$ being as defined in the general formula (I).

Among the compounds of general formula (I) that are subjects of the invention, a second subgroup of compounds is constituted by the compounds for which $X_1$, $X_2$, $X_3$ and $X_4$ represent, independently of each other, a nitrogen atom or a group $C$—$R_1$;

it being understood that one from among $X_1$, $X_2$, $X_3$ and $X_4$ represents a nitrogen atom, the others corresponding to a group $C$—$R_1$;

$R_1$ being as defined in the general formula (I).

Among the compounds of general formula (I) that are subjects of the invention, a third subgroup of compounds is constituted by the compounds for which $X_1$, $X_2$ and $X_3$ represent a group $C$—$R_1$; $X_4$ represents a nitrogen atom;

$R_1$ being as defined in the general formula (I).

Among the compounds of general formula (I) that are subjects of the invention, a fourth subgroup of compounds is constituted by the compounds for which $R_1$ is chosen from a hydrogen atom, a halogen atom, more particularly a fluorine atom, and a group $C_1$-$C_6$-fluoroalkyl, more particularly a trifluoromethyl group.

Among the compounds of general formula (I) that are subjects of the invention, a fifth subgroup of compounds is constituted by the compounds for which n is equal to 1.

Among the compounds of general formula (I) that are subjects of the invention, a sixth subgroup Y represents an aryl, more particularly a phenyl, optionally substituted with one or more halogen atoms, more particularly fluorine atoms.

Among the compounds of general formula (I) that are subjects of the invention, a seventh subgroup of compounds is constituted by the compounds for which W represents an oxygen atom.

Among the compounds of general formula (I) that are subjects of the invention, an eighth subgroup of compounds is constituted by the compounds for which A represents a bicyclic heteroaryl of formula:

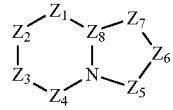

in which $Z_1$, $Z_2$, $Z_3$ and $Z_4$ represent, independently of each other, a carbon atom or a nitrogen atom;

$Z_5$, $Z_6$ and $Z_7$ represent, independently of each other, a nitrogen atom or a group $C$—$R_{2b}$;

$Z_8$ represents a carbon atom;

two, at most, from among $Z_1$, $Z_2$, $Z_3$, $Z_4$, $Z_5$, $Z_6$ and $Z_7$ represent a nitrogen atom;

one from among $Z_1$, $Z_2$, $Z_3$ and $Z_4$, corresponding to a carbon atom, being bonded to the nitrogen atom of the amide or thioamide of formula (I);

$R_{2b}$ being as defined in the general formula (I).

Among the compounds of general formula (I) that are subjects of the invention, a ninth subgroup of compounds is constituted by the compounds for which A represents a bicyclic heteroaryl of formula:

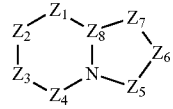

in which $Z_1$, $Z_2$, $Z_3$ and $Z_4$ represent, independently of each other, a carbon atom or a nitrogen atom;

$Z_5$, $Z_6$ and $Z_7$ represent, independently of each other, a nitrogen atom or a group $C$—$R_{2b}$;

$Z_8$ represents a carbon atom;

two, at most, from among $Z_1$, $Z_2$, $Z_3$, $Z_4$, $Z_5$, $Z_6$ and $Z_7$ represent a nitrogen atom;

one from among $Z_1$, $Z_2$, $Z_3$ and $Z_4$, corresponding to a carbon atom, being bonded to the nitrogen atom of the amide or thioamide of formula (I);

$R_{2b}$ represents a hydrogen atom or a group $C_1$-$C_6$-alkyl, $C(O)O$—$C_1$-$C_6$-alkyl, phenyl or thienyl; the groups $C_1$-$C_6$-alkyl possibly being substituted with a hydroxyl or $C_1$-$C_6$-alkoxy group.

Among the compounds of general formula (I) that are subjects of the invention, a tenth subgroup of compounds is constituted by the compounds for which A represents a bicyclic heteroaryl of formula:

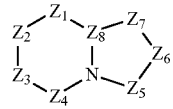

in which $Z_1$, $Z_2$, $Z_3$ and $Z_4$ represent, independently of each other, a carbon atom or a nitrogen atom;

$Z_5$, $Z_6$ and $Z_7$ represent, independently of each other, a nitrogen atom or a group $C$—$R_{2b}$;

$Z_8$ represents a carbon atom;

two, at most, from among $Z_1$, $Z_2$, $Z_3$, $Z_4$, $Z_5$, $Z_6$ and $Z_7$ represent a nitrogen atom;

one from among $Z_1$, $Z_2$, $Z_3$ and $Z_4$, corresponding to a carbon atom, being bonded to the nitrogen atom of the amide or thioamide of formula (I);

$R_{2b}$ represents a hydrogen atom or a methyl, ethyl, tert-butyl, C(O)O-ethyl, phenyl or thienyl group; the methyl groups possibly being substituted with a hydroxyl or methoxy group.

Among the compounds of general formula (I) that are subjects of the invention, an eleventh subgroup of compounds is constituted by the compounds for which A represents the group

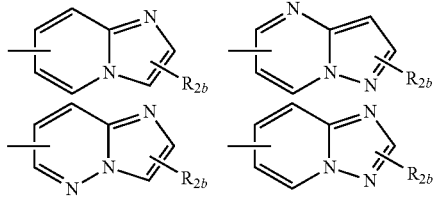

$R_{2b}$ being as defined in the general formula (I).

Among the compounds of general formula (I) that are subjects of the invention, a twelfth subgroup of compounds is constituted by the compounds for which A represents the group

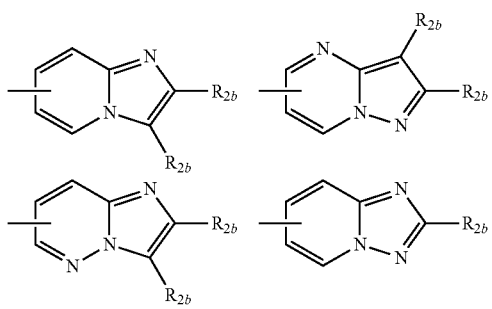

$R_{2b}$ represents a hydrogen atom or a group $C_1$-$C_6$-alkyl, C(O)O—$C_1$-$C_6$-alkyl, phenyl or thienyl; the groups $C_1$-$C_6$-alkyl possibly being substituted with a hydroxyl or $C_1$-$C_6$-alkoxy group.

Among the compounds of general formula (I) that are subjects of the invention, a thirteenth subgroup of compounds is constituted by the compounds for which A represents the group

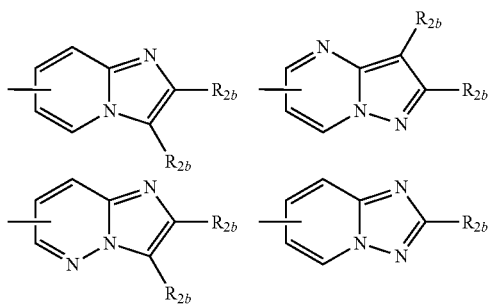

$R_{2b}$ represents a hydrogen atom or a methyl, ethyl, tert-butyl, C(O)O-ethyl, phenyl or thienyl group; the methyl groups possibly being substituted with a hydroxyl or methoxy group.

Among the compounds of general formula (I) that are subjects of the invention, a fourteenth subgroup of compounds is constituted by the compounds for which A represents the group

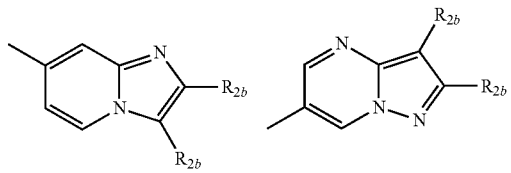

$R_{2b}$ being as defined in the general formula (I).

Among the compounds of general formula (I) that are subjects of the invention, a fifteenth subgroup of compounds is constituted by the compounds for which A represents the group

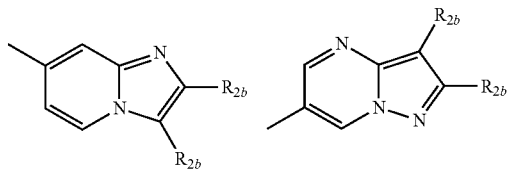

$R_{2b}$ represents a hydrogen atom or a group $C_1$-$C_6$-alkyl, phenyl or thienyl; the groups $C_1$-$C_6$-alkyl possibly being substituted with a hydroxyl or $C_1$-$C_6$-alkoxy group.

Among the compounds of general formula (I) that are subjects of the invention, a sixteenth subgroup of compounds is constituted by the compounds for which A represents the group

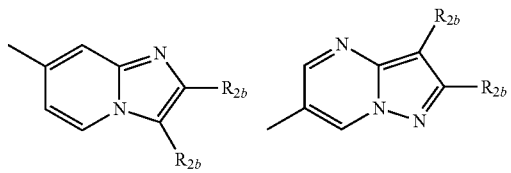

$R_{2b}$ represents a hydrogen atom or a methyl, ethyl, tert-butyl, phenyl or thienyl group;

the methyl groups possibly being substituted with a hydroxyl or methoxy group.

Among the compounds of general formula (I) that are subjects of the invention, a seventeenth subgroup of compounds is constituted by the compounds for which the definitions of $X_1$, $X_2$, $X_3$, $X_4$, n, Y, W and A given above are combined.

Among the compounds of general formula (I) that are subjects of the invention, an eighteenth subgroup of compounds is constituted by the compounds for which $X_1$, $X_2$, $X_3$ and $X_4$ represent, independently of each other, a group C—$R_1$; or alternatively $X_1$, $X_2$ and $X_3$ represent a group C—$R_1$; $X_4$ represents a nitrogen atom;

$R_1$ is chosen from a hydrogen atom, a halogen atom, more particularly a fluorine atom, and a group $C_1$-$C_6$-fluoroalkyl, more particularly a trifluoromethyl group;

n is equal to 1;

Y represents an aryl, more particularly a phenyl, optionally substituted with one or more halogen atoms, more particularly fluorine atoms;

W represents an oxygen atom;

A represents a bicyclic heteroaryl of formula:

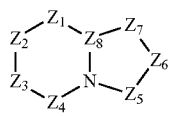

in which $Z_1$, $Z_2$, $Z_3$ and $Z_4$ represent, independently of each other, a carbon atom or a nitrogen atom;

$Z_5$, $Z_6$ and $Z_7$ represent, independently of each other, a nitrogen atom or a group C—$R_{2b}$;

$Z_8$ represents a carbon atom;

two, at most, from among $Z_1$, $Z_2$, $Z_3$, $Z_4$, $Z_5$, $Z_6$ and $Z_7$ represent a nitrogen atom;

one from among $Z_1$, $Z_2$, $Z_3$ and $Z_4$, corresponding to a carbon atom, being bonded to the nitrogen atom of the amide or thioamide of formula (I);

$R_{2b}$ represents a hydrogen atom or a group $C_1$-$C_6$-alkyl, C(O)O—$C_1$-$C_6$-alkyl, phenyl or thienyl; the groups $C_1$-$C_6$-alkyl possibly being substituted with a hydroxyl or $C_1$-$C_6$-alkoxy group.

Among the compounds of general formula (I) that are subjects of the invention, mention may be made especially of the following compounds:

1• N-(2,3-Dimethylimidazo[1,2-a]pyrid-7-yl)-5-fluoro-1-[(3-fluorophenyl)methyl]-1H-indole-2-carboxamide;

2• N-(2,3-Dimethylimidazo[1,2-a]pyrid-6-yl)-5-fluoro-1-[(3-fluorophenyl)methyl]-1H-indole-2-carboxamide;

3• N-[2-(Hydroxymethyl)imidazo[1,2-a]pyrid-6-yl]-5-fluoro-1-[(3-fluorophenyl)-methyl]-1H-indole-2-carboxamide;

4• N-(3-Methyl-2-phenylimidazo[1,2-a]pyrid-6-yl)-5-fluoro-1-[(3-fluorophenyl)-methyl]-1H-indole-2-carboxamide;

5• N-(2-Ethylimidazo[1,2-a]pyrid-6-yl)-5-fluoro-1-[(3-fluorophenyl)methyl-1H-indole-2-carboxamide;

6• N-[2-(Thien-2-yl)imidazo[1,2-a]pyrid-6-yl]-5-fluoro-1-[(3-fluorophenyl)methyl]-1H-indole-2-carboxamide;

7• N-(2-tert-Butylimidazo[1,2-a]pyrid-6-yl)-5-fluoro-1-[(3-fluorophenyl)methyl]-1H-indole-2-carboxamide;

8• N-(2-Methoxymethylimidazo[1,2-a]pyrid-7-yl)-5-fluoro-1-[(3-fluorophenyl)-methyl]-1H-indole-2-carboxamide;

9• N-[2-(Hydroxymethyl)imidazo[1,2-a]pyrid-7-yl]-5-fluoro-1-[(3-fluorophenyl)-methyl]-1H-indole-2-carboxamide;

10• N-(2-Methyl-3-phenylimidazo[1,2-a]pyrid-7-yl)-5-fluoro-1-[(3-fluorophenyl)-methyl]-1H-indole-2-carboxamide;

11• N-[2-(Thien-2-yl)imidazo[1,2-a]pyrid-7-yl]-5-fluoro-1-[(3-fluorophenyl)methyl]-1H-indole-2-carboxamide;

12• N-(2-Ethylimidazo[1,2-a]pyrid-7-yl)-5-fluoro-1-[(3-fluorophenyl)methyl-1H-indole-2-carboxamide;

13• N-(2-tert-Butylimidazo[1,2-a]pyrid-7-yl)-5-fluoro-1-[(3-fluorophenyl)methyl]-1H-indole-2-carboxamide;

14• N-(2,3-Dimethylimidazo[1,2-a]pyrid-7-yl)-5-trifluoromethyl-1-[(3-fluorophenyl)-methyl]-1H-indole-2-carboxamide;

15• N-(2-Ethylimidazo[1,2-a]pyrid-7-yl)-5-trifluoromethyl-1-[(3-fluorophenyl)methyl]-1H-pyrrolo[2,3-b]pyridine-2-carboxamide;

16• N-(2,3-Dimethylimidazo[1,2-a]pyrid-7-yl)-5-trifluoromethyl-1-[(3-fluorophenyl)-methyl]-1H-pyrrolo[2,3-b]pyridine-2-carboxamide;

17• N-[2-(Hydroxymethyl)imidazo[1,2-a]pyrid-7-yl]-5-trifluoromethyl-1-[(3-fluoro-phenyl)methyl]-1H-indole-2-carboxamide;

18• N-[2-(Hydroxymethyl)imidazo[1,2-a]pyrid-7-yl]-5-trifluoromethyl-1-[(3-fluoro-phenyl)methyl]-1H-pyrrolo[2,3-b]pyridine-2-carboxamide;

19• N-(2-Methylimidazo[1,2-a]pyrid-7-yl)-5-fluoro-1-[(3-fluorophenyl)methyl]-1H-indole-2-carboxamide;

20• N-(2-Methylpyrazolo[1,5-a]pyrimidin-6-yl)-5-fluoro-1-[(3-fluorophenyl)methyl]-1H-indole-2-carboxamide;

21• N-[2-(Ethyloxycarbonyl)imidazo[1,2-b]pyridazin-6-yl]-5-fluoro-1-[(3-fluoro-phenyl)methyl]-1H-indole-2-carboxamide;

22• N-[(2-(Ethyloxycarbonyl)imidazo[1,2-a]pyrid-6-yl)-5-fluoro-1-[(3-fluorophenyl)-methyl]-1H-indole-2-carboxamide;

23• N-(2-Methylimidazo[1,2-a]pyrid-6-yl)-5-fluoro-1-[(3-fluorophenyl)methyl]-1H-indole-2-carboxamide;

24• N-([1,2,4]Triazolo[1,5-a]pyrid-6-yl)-5-fluoro-1-[(3-fluorophenyl)methyl]-1H-2-carboxamide.

Among the compounds of general formula (I) that are subjects of the invention, one subfamily is represented by the compounds of general formula (I') for which:

$R_{2b}$ represents a hydrogen atom, a halogen atom or a group $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl, $C_1$-$C_6$-alkoxy, hydroxyl, thiol, oxo, thio, $C_3$-$C_7$-cycloalkyloxy, $C_1$-$C_6$-fluoroalkoxy, $C_3$-$C_7$-cycloalkyl-$C_1$-$C_3$-alkylenoxy, $C_1$-$C_6$-alkoxy-$C_1$-$C_3$-alkylene, $C_3$-$C_7$-cycloalkyloxy-$C_1$-$C_3$-alkylene, $C_3$-$C_7$-cycloalkyl-$C_1$-$C_3$-alkylenoxy-$C_1$-$C_3$-alkylene, $C_1$-$C_6$-alkyl-C(O)—O—$C_1$-$C_3$-alkylene, $C_1$-$C_6$-alkyl-C(O)—O—, $C_3$-$C_7$-cycloalkyl-C(O)—O—$C_1$-$C_3$-alkylene, $C_3$-$C_7$-cycloalkyl-C(O)—O—, $C_1$-$C_6$-fluoroalkyl-C(O)—O—$C_1$-$C_3$-alkylene, $C_1$-$C_6$-fluoroalkyl-C(O)—O—, C(O)NR$_3$R$_4$, C(O)O—$C_1$-$C_6$-alkyl, cyano, CHO, $CO_2H$, —C(O)—$C_1$-$C_6$-alkyl or —C(O)—$C_3$-$C_7$-cycloalkyl; the groups $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl, $C_1$-$C_6$-alkoxy, $C_3$-$C_7$-cycloalkyloxy, $C_1$-$C_6$-fluoroalkoxy, $C_3$-$C_7$-cycloalkyl-$C_1$-$C_3$-alkylenoxy, $C_1$-$C_6$-alkoxy-$C_1$-$C_3$-alkylene, $C_3$-$C_7$-cycloalkyloxy-$C_1$-$C_3$-alkylene and $C_3$-$C_7$-cycloalkyl-$C_1$-$C_3$-alkylenoxy-$C_1$-$C_3$-alkylene possibly being substituted with a hydroxyl, $C_1$-$C_6$-alkoxy or NR$_3$R$_4$ group;

$R_3$ and $R_4$ being as defined in the general formula (I).

Among the compounds of general formula (I') that are subjects of the invention, a first subgroup of compounds is constituted by the compounds for which $X_1$, $X_2$, $X_3$ and $X_4$ represent, independently of each other, a group C—$R_1$; and $R_1$ is chosen from a hydrogen atom, a halogen atom, more particularly a fluorine atom, and a group $C_1$-$C_6$-fluoroalkyl, more particularly a trifluoromethyl group.

Among the compounds of general formula (I') that are subjects of the invention, a second subgroup of compounds is constituted by the compounds for which n is equal to 1 and Y represents an aryl, more particularly a phenyl, optionally substituted with one or more halogen atoms, more particularly fluorine atoms.

Among the compounds of general formula (I') that are subjects of the invention, a third subgroup of compounds is constituted by the compounds for which W represents an oxygen atom.

Among the compounds of general formula (I') that are subjects of the invention, a fourth subgroup of compounds is constituted by the compounds for which A represents the group

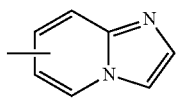

this group being optionally substituted as defined in the general formula (I) above.

Among the compounds of general formula (I') that are subjects of the invention, a fifth subgroup of compounds is constituted by the compounds for which $X_1$, $X_2$, $X_3$ and $X_4$ represent, independently of each other, a group C—$R_1$; and $R_1$ is chosen from a hydrogen atom, a halogen atom, more particularly a fluorine atom, and a group $C_1$-$C_6$-fluoroalkyl, more particularly a trifluoromethyl group;

n is equal to 1;

Y represents an aryl, more particularly a phenyl, optionally substituted with one or more halogen atoms, more particularly fluorine atoms;

W represents an oxygen atom;

A represents the group

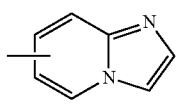

this group being optionally substituted as defined in the general formula (I) above.

In the text hereinbelow, the term "leaving group" means a group that can be readily cleaved from a molecule by breaking a heterolytic bond, with loss of an electron pair. This group may thus be readily replaced by another group during a substitution reaction, for example. Such leaving groups are, for example, halogens or an activated hydroxyl group such as a methanesulfonate, benzenesulfonate, p-toluenesulfate, trifluoromethanesulfonate, acetate, etc. Examples of leaving groups and references for preparing them are given in "Advances in Organic Chemistry", J. March, 5th Edition, Wiley Interscience, 2001.

In the text hereinbelow, the term "protecting group" means a group that can be momentarily incorporated into a chemical structure for the purpose of temporarily inactivating a part of the molecule during a reaction, and which may be readily removed in a subsequent synthetic step. Examples of protecting groups and references concerning their properties are given in T. W. Greene, P. G. M. Wutz, 3rd Edition, Wiley Interscience 1999.

In accordance with the invention, the compounds of general formula (I) may be prepared according to the process illustrated by the general schemes 1 and 2 below:

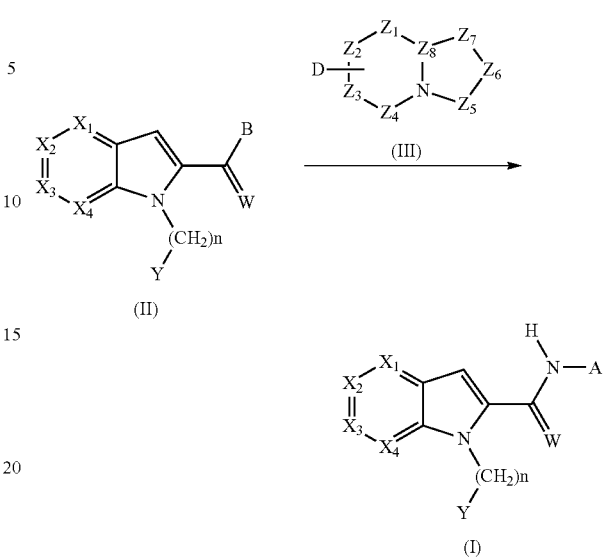

Scheme 1

According to scheme 1, compounds (I) may be obtained by reacting a compound of general formula (II), in which B represents an $NH_2$ group and $X_1$, $X_2$, $X_3$, $X_4$, n, Y and W are as defined in the general formula (I) above, with a compound of general formula (III), in which $Z_1$, $Z_2$, $Z_3$, $Z_4$, $Z_5$, $Z_6$, $Z_7$ and $Z_8$ are as defined in the general form above and D represents a leaving group, as defined above, for instance a bromine or iodine atom or a trifluoromethanesulfonate group, for example according to a method similar to that described in *J. Am. Chem. Soc.* 2001, 123 (31), 7727, or according to methods described in the literature or known to those skilled in the art, in the presence of a copper salt in catalytic amount, in the presence of a catalytic amount of a copper ligand, such as a diamine, the whole in the presence of a base such as potassium carbonate, in a solvent such as dioxane;

for example according to a method similar to that described in *J. Am. Chem. Soc.* 2002, 124 (21), 6043, or according to methods described in the literature or known to those skilled in the art, in the presence of a catalytic amount of a palladium derivative, such as palladium diacetate, in the presence of a catalytic amount of a palladium ligand, such as a diphosphine, the whole in the presence of a base such as caesium carbonate, at reflux in a solvent such as dioxane.

The compounds of general formula (I) may also be obtained by reacting a compound of general formula (II), in which B represents a hydroxyl group and $X_1$, $X_2$, $X_3$, $X_4$, n, Y and W are as defined in the general formula (I) above, with a compound of general formula (III), in which $Z_1$, $Z_2$, $Z_3$, $Z_4$, $Z_5$, $Z_6$, $Z_7$ and $Z_8$ are as defined in the general formula (I) above and D represents an $NH_2$ group, in the presence of a coupling agent such as diethyl cyanophosphonate or N-(3-dimethylaminopropyl)-N'-ethylcarbodiimide, optionally in the presence of a base such as triethylamine, in a solvent, for instance dimethylformamide.

The compounds of general formula (I) may also be obtained by reacting a compound of general formula (II), in which B is a chlorine atom and $X_1$, $X_2$, $X_3$, $X_4$, n, Y and W are as defined in the general formula (I) above, with a compound of general formula (III), in which $Z_1$, $Z_2$, $Z_3$, $Z_4$, $Z_5$, $Z_6$, $Z_7$ and $Z_8$ are as defined in the general formula (I) above and D represents an $NH_2$ group, in a solvent such as dichloroethane, toluene or tetrahydrofuran.

The compounds of general formula (II), for which B represents a group $C_1$-$C_6$-alkoxyl, may be converted into compounds of general formula (II), in which B represents a hydroxyl group, via the action of a base such as sodium hydroxide or potassium hydroxide in solution in a solvent such as ethanol. The compounds of general formula (II), in which B represents a hydroxyl group may, thereafter, be converted into compounds of general formula (II), in which B represents a chlorine atom, via the action of a chlorinating agent such as thionyl chloride in a solvent such as dichloromethane.

Alternatively, according to scheme 2, the compounds of general formula (I), in which W represents an oxygen atom and A represents a group:

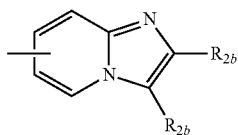

may be obtained by reacting a compound of general formula (V) in which $X_1$, $X_2$, $X_3$, $X_4$, n and Y are as defined in the general formula (I) above and PG represents a hydrogen atom, with a compound of general formula (IV), in which X represents a leaving group, as defined above, for instance a bromine or chlorine atom and $R_{2b}$ is as defined in the general formula (I) above, for example according to a method similar to those described in *J. Org. Chem.* 1965, 30 (7), 2403 and *Organometallics* 2008, 27(8), 1936 or according to methods described in the literature or known to those skilled in the art.

The compounds of general formula (V), in which PG represents a hydrogen atom, may be obtained from compounds of general formula (V), in which PG represents a protecting group, for example an acetyl group, according to deprotection methods described in the literature or known to those skilled in the art.

The compounds of general formula (V) in which PG represents a protecting group, for example an acetyl group, may be obtained by reacting a compound of general formula (II), in which B represents an $NH_2$ group and $X_1$, $X_2$, $X_3$, $X_4$, n and Y are as defined in the general formula (I) above, with a compound of general formula (VI), in which PG represents a protecting group, for example an acetyl group, and D represents a leaving group, as defined above, for instance a bromine atom or a trifluoromethanesulfonate group, for example according to a method similar to that described in *J. Am. Chem. Soc.* 2001, 123 (31), 7727, or according to methods described in the literature or known to those skilled in the art, in the presence of a copper salt in catalytic amount, in the presence of a catalytic amount of a copper ligand, such as a diamine, the whole in the presence of a base, such as potassium carbonate, in a solvent such as dioxane.

The compounds of general formula (V) may also be obtained by reacting a compound of general formula (II), in which B represents a hydroxyl group and $X_1$, $X_2$, $X_3$, $X_4$, n and Y are as defined in the general formula (I) above, with a compound of general formula (VI), in which PG represents a protecting group, for example an acetyl group, and D represents an amino group, according to any coupling method known to those skilled in the art.

According to another of its aspects, a subject of the invention is also the compounds of formulae (IIIa), (IIIb), (IIIc), (IIId), (IIIe) and (IIIf). These compounds are useful as synthetic intermediates for the preparation of the compounds of formula (I).

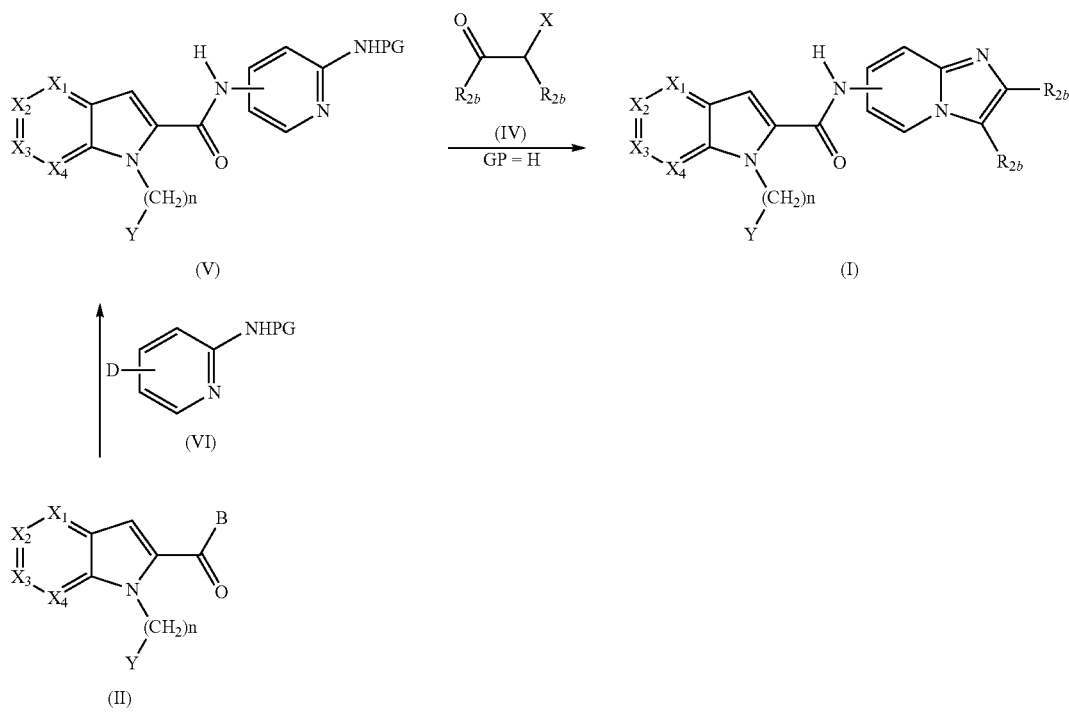

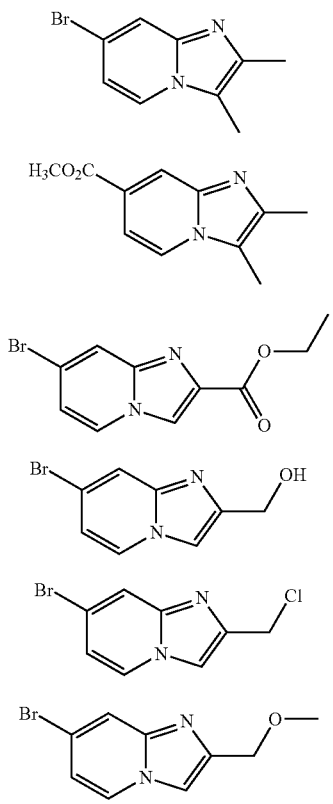

The compounds of formulae (IIIa), (IIIb), (IIIc), (IIId), (IIIe) and (IIIf) may be prepared, for example, according to the processes described in Examples 1, 8 and 14.

In schemes 1 and 2, the compounds of general formulae (II), (III), (IV) and (VI) the other reagents, when their preparation is not described, are commercially available, described in the literature or prepared by analogy with processes described in the literature (U.S. Pat. No. 6,737,435; U.S. Pat. No. 6,673,797; WO 2006/101455; Synthesis 1985, 2, 186; J. G. Lombardino J. Org. Chem. 1965, 30 (7), 2403; T. M. Williams J. Med. Chem. 1993, 36 (9), 1291; J. Med. Chem. 2008, 51 (19), 6044; JP 2001-151 771 A2; WO 2006/024776; WO 2006/072736; WO 2007/010144; WO 2007/010138, for example).

The compounds of general formula (I), for which one from among $X_1$, $X_2$, $X_3$ and $X_4$ corresponds to a carbon atom substituted with an alkyl group, may be obtained via a coupling reaction, catalysed with a metal such as palladium or iron, performed on the corresponding compounds of general formula (I), substituted with a halogen atom, such as a chlorine, in the presence, for example, of an alkylmagnesium halide or an alkylzinc halide, according to methods described in the literature (A. Furstner et al., J. Am. Chem. Soc. 2002, 124(46), 13856; G. Quéguiner et al., J. Org. Chem. 1998, 63(9), 2892), for example, or known to those skilled in the art.

The compounds of general formula (I), for which one from among $X_1$, $X_2$, $X_3$ and $X_4$ corresponds to a carbon atom substituted with a cyano, aryl or heteroaryl group, may be obtained via a coupling reaction, catalysed with a metal such as palladium, performed on the corresponding compounds of general formula (I), substituted, for example, with a bromine atom, in the presence of trimethylsilyl cyanide, an arylboronic acid or a heteroarylboronic acid, or via any other method described in the literature or known to those skilled in the art.

The compounds of general formula (I) substituted with a group $C(O)NR_3R_4$ may be obtained from the corresponding compounds of general formula (I) substituted with a cyano group, according to methods described in the literature or known to those skilled in the art.

The compounds of general formula (I) substituted with a group —S(O)-alkyl or —S(O)$_2$-alkyl may be obtained by oxidation of the corresponding compounds of general formula (I), substituted with a group thioalkyl, according to methods described in the literature or known to those skilled in the art.

The compounds of general formula (I), substituted with a group $NR_3R_4$, $NR_5COR_6$ or $NR_5SO_2R_7$ may be obtained from the corresponding compounds of general formula (I), substituted with a nitro group, for example via reduction, followed by acylation or sulfonylation, according to methods described in the literature or known to those skilled in the art.

The compounds of general formula (I) in which W represents a sulfur atom may be obtained, for example, by reacting the corresponding compounds of general formula (I), in which W represents an oxygen atom, with a reagent such as Lawesson's reagent.

The compounds of general formula (I) for which $R_{2b}$ corresponds to a hydroxyalkyl group may be obtained from compounds of general formula (I) for which $R_{2b}$ corresponds, for example, to an acetoxyalkyl or pivaloyloxyalkyl group, according to chemical methods known to those skilled in the art, such as reaction with a base such as an aqueous sodium hydroxide solution, or reaction with an alkoxide, for example methoxide, of a salt such as lithium or sodium, in an alcoholic solvent such as methanol or ethanol.

The compounds of general formula (I) for which $R_{2b}$ corresponds to a hydroxymethyl group may also be obtained from compounds of general formula (I) for which $R_{2b}$ corresponds, for example, to an ethyl carboxylate group, by reaction with a reducing agent such as sodium borohydride, in a solvent such as tetrahydrofuran.

The compounds of general formula (II), for which one from among $X_1$, $X_2$, $X_3$ and $X_4$ corresponds to a carbon atom substituted with a group $NR_3R_4$, $NR_5COR_6$ or $NR_5SO_2R_7$ and B represents a group $C_1$-$C_6$-alkoxy, $C_3$-$C_7$-cycloalkyloxy, $C_3$-$C_7$-cycloalkyl-$C_1$-$C_3$-alkylenoxy or aryl-$C_1$-$C_3$-alkylenoxy, may be obtained from the corresponding compounds of general formula (II), substituted, for example, with a bromine atom, via a coupling reaction with an amine, an amide or a sulfonamide, respectively, in the presence of a base, a phosphine and a palladium-based catalyst, according to methods described in the literature or known to those skilled in the art.

The compounds of general formula (II), for which one from among $X_1$, $X_2$, $X_3$ and $X_4$ corresponds to a carbon atom substituted with a group $SO_2NR_3R_4$ and B represents a group $C_1$-$C_6$-alkoxy, $C_3$-$C_7$-cycloalkyloxy, $C_3$-$C_7$-cycloalkyl-$C_1$-$C_3$-alkylenoxy or aryl-$C_1$-$C_3$-alkylenoxy, may be obtained via a method similar to that described in Pharmazie 1990, 45, 346, or according to methods described in the literature or known to those skilled in the art.

The examples that follow describe the preparation of certain compounds in accordance with the invention. These examples are not limiting, and serve merely to illustrate the present invention. The numbers of the illustrated compounds refer to those in Table 1. The elemental microanalyses, the LC-MS analyses (liquid chromatography coupled to mass spectrometry) and the IR or NMR spectrum confirm the structures of the compounds obtained.

EXAMPLE 1

Compound 1

N-(2,3-Dimethylimidazo[1,2-a]pyrid-7-yl)-5-fluoro-1-[(3-fluorophenyl)methyl]-1H-indole-2-carboxamide

1.1 5-Fluoro-1-[(3-fluorophenyl)methyl]-1H-indole-2-carboxylic acid

An aqueous sodium hydroxide solution, prepared from 1.15 g (28.92 mmol) of sodium hydroxide pellets in 50 mL of water, is added to a solution of 7.6 g (24.10 mmol) of ethyl 5-fluoro-1-[(3-fluorophenyl)methyl]-1H-indole-2-carboxylate (WO 2006/024776) in 241 mL of ethanol. The mixture is heated for two hours and then concentrated under reduced pressure. The resulting solid is taken up in 200 mL of water. The solution is washed with twice 100 mL of ethyl ether, acidified by successive addition of small amounts of concentrated hydrochloric acid and then extracted with 200 mL of ethyl acetate. The organic phase is finally washed twice with 100 mL of water, once with 50 ml of saturated sodium chloride solution, dried over magnesium sulfate and concentrated under reduced pressure. After drying at 50° C. under reduced pressure, 6.4 g of the expected product are obtained in the form of a solid, which is used without further purification in the rest of the synthesis.

1.2 5-fluoro-1-[(3-fluorophenyl)methyl]-1H-indole-2-carboxamide

To a suspension, stirred at 20° C., of 2 g (6.96 mmol) of 5-fluoro-1-[(3-fluorophenyl)-methyl]-1H-indole-2-carboxylic acid, prepared in step 1.1, in 80 mL of dry toluene are added 5.08 mL (69.62 mmol) of thionyl chloride. The reaction mixture is refluxed for 2 hours with stirring and is then concentrated under reduced pressure. The resulting product is taken up in 10 mL of dichloromethane, and this solution is poured dropwise into a solution of 9.12 mL (69.62 mmol) of 30% aqueous ammonia. The reaction mixture is stirred for 14 hours at 20° C. After this time, a solid is collected by filtration, and is triturated in 50 mL of diisopropyl ether. After filtering off and drying under reduced pressure, 0.58 g of the expected product is collected.

$^1$H NMR (DMSO-D$_6$), δ ppm: 8.11 (broad peak, 1H); 7.5 (m, 3H); 7.32 (m, 1H); 7.25 (s, 1H); 7.09 (m, 2H); 6.89 (m, 2H); 5.91 (s, 2H).

1.3 7-Bromo-2,3-dimethylimidazo[1,2-a]pyridine (Compound IIIa)

3 mL (19.86 mmol) of 3-bromobutan-2-one are added to a mixture, stirred at 20° C., of 1.5 g (8.67 mmol) of 2-amino-4-bromopyridine and 1.45 g (17.34 mmol) of sodium hydrogen carbonate in 50 mL of ethanol. The mixture is stirred at reflux for 12 hours and then concentrated under reduced pressure. The mixture obtained is taken up in 20 mL of water. The pH of the solution is basified by successive addition of potassium carbonate. A precipitate is collected by filtration, and is washed with water and then dried under reduced pressure. 0.79 g of the expected product is thus isolated, and is used without further purification in the rest of the synthesis.

$^1$H NMR (DMSO-D$_6$), δ ppm: 8.15 (d, 1H); 7.71 (s, 1H); 7.01 (d, 1H); 2.39 (s, 3H); 2.31 (s, 3H).

1.4 N-(2,3-Dimethylimidazo[1,2-a]pyrid-7-yl)-5-fluoro-1-[(3-fluorophenyl)methyl]-1H-indole-2-carboxamide (compound 1)

0.0134 g (0.07 mmol) of copper iodide, 0.2 g (0.7 mmol) of 5-fluoro-1-[(3-fluorophenyl)-methyl]-1H-indole-2-carboxamide, obtained in step 1.2, 132 mg (0.56 mmol) of 7-bromo-2,3-dimethylimidazo[1,2-a]pyridine, obtained in step 1.3, 193 mg (1.4 mmol) of potassium carbonate and 5 mL of dioxane are mixed together in a pressure tube, under an inert atmosphere at 20° C. The suspension is degassed for a few minutes, 0.01 mL (0.08 mmol) of trans-1,2-cyclohexanediamine is then added and the tube is closed. The reaction mixture is stirred for 20 hours at 110° C. After this time, the cooled suspension is filtered through a pad of silica, eluting with a mixture of dichloromethane and methanol. The filtrate is concentrated under reduced pressure. The resulting product is triturated in a mixture of 90 mL of isopropanol and 10 mL of isopropyl ether. A solid is collected by filtration, and is purified by chromatography on a column of silica, eluting with a mixture of dichloromethane and methanol. 27 mg of the expected product are thus obtained.

m.p.: 251-253° C.

$^1$H NMR (DMSO-D$_6$), δ ppm: 10.82 (s, 1H); 8.41 (broad peak, 1H); 8.19 (broad peak, 1H); 7.62 (dxd, 1H); 7.58 (dxd, 1H); 7.51 (s, 1H); 7.45 (d, 1H); 7.32 (m, 1H); 7.19 (txd, 1H); 7.4 (txd, 1H); 6.5 (m, 2H); 5.89 (s, 2H); 2.5 (s, 6H).

EXAMPLE 2

Compound 2

N-(2,3-Dimethylimidazo[1,2-a]pyrid-6-yl)-5-fluoro-1-[(3-fluorophenyl)methyl]-1H-indole-2-carboxamide

2.1 6-Bromo-2,3-dimethylimidazo[1,2-a]pyridine 13.53 mL (130.06 mmol) of 3-bromobutan-2-one are added to a mixture, stirred at 20° C., of 5 g (28.90 mmol) of 2-amino-5-bromopyridine and 4.85 g (57.80 mmol) of sodium hydrogen carbonate in 100 mL of ethanol. The mixture is refluxed for 12 hours and then concentrated under reduced pressure. The mixture obtained is taken up in 100 mL of water. The pH of the solution is basified by successive additions of potassium carbonate. The mixture is then extracted with 3×50 mL of ethyl acetate. The combined organic phases are washed with water (50 mL), dried over sodium sulfate and then concentrated under reduced pressure. An oil is obtained, which is purified by chromatography on a column of silica, eluting with a mixture of dichloromethane and methanol. 1.1 g of the expected product are thus isolated.

$^1$H NMR (DMSO-D$_6$), δ ppm: 8.5 (s, 1H); 7.4 (d, 1H); 7.25 (d, 1H); 2.4 (s, 3H); 2.31 (s, 3H).

LC-MS: 225 ([M+H]+, Rt=0.52 min.).

2.2 N-(2,3-Dimethylimidazo[1,2-a]pyrid-6-yl)-5-fluoro-1-[(3-fluorophenyl)methyl]-1H-indole-2-carboxamide (compound 2)

0.054 g (0.28 mmol) of copper iodide, 0.8 g (2.79 mmol) of 5-fluoro-1-[(3-fluorophenyl)-methyl]-1H-indole-2-carboxamide, obtained in step 1.2, 0.5 g (2.24 mmol) of 6-bromo-2,3-dimethylimidazo[1,2-a]pyridine, obtained in step 2.1, 0.77 g (5.59 mmol) of potassium carbonate and 25 mL of dioxane are mixed together in a pressure tube, under an inert atmosphere at 20° C. The suspension is degassed for a few minutes, 0.04 mL (0.31 mmol) of trans-1,2-cyclohexanediamine is then added and the tube is closed. The reaction mixture is stirred for 20 hours at 110° C. After this time, the reaction mixture is diluted with 50 mL of water and 50 mL of ethyl acetate. The aqueous phase is extracted with 2×50 mL of ethyl acetate. The combined organic phases are washed with water (50 mL), dried over sodium sulfate and then concentrated under reduced pressure. The resulting product is triturated in a boiling mixture of 30 mL of isopropyl ether and 10 mL of water. 0.63 g of the expected product is collected by filtration while hot, in the form of a white solid.

m.p.: 220-242° C.

$^1$H NMR (DMSO-D$_6$), δ ppm: 11.0 (s, 1H); 9.2 (s, 1H); 8.1 (m, 1H); 7.95 (m, 1H); 7.6 (m, 2H); 7.55 (s, 1H); 7.35 (m, 1H); 7.2 (m, 1H); 7.15 (m, 1H); 6.9 (m, 2H); 5.9 (s, 2H); 2.5 (s, 3H); 2.45 (s, 3H).

EXAMPLE 3

Compound 3

N-[2-(Hydroxymethylimidazo[1,2-a]pyrid-6-yl]-5-fluoro-1-[(3-fluorophenyl)methyl]-1H-indole-2-carboxamide 20 mg (0.1 mmol) of copper iodide, 0.3 g (1.05 mmol) of 5-fluoro-1-[(3-fluorophenyl)-methyl]-1H-indole-2-carboxamide, obtained in step 1.2, 0.23 g (0.84 mmol) of 6-iodoimidazo[1,2-a]pyrid-2-ylmethanol, 0.29 g (2.1 mmol) of potassium carbonate and 10 mL of dioxane are mixed together in a pressure tube, under an inert atmosphere at 20° C. The suspension is degassed for a few minutes, 0.01 mL (0.12 mmol) of trans-1,2-cyclohexanediamine is then added and the tube is closed. The reaction mixture is stirred for 15 hours at 110° C. After this time, the suspension, cooled to room temperature and is poured into 20 mL of water and 20 mL of ethyl acetate. The aqueous phase is extracted with 2×10 mL of ethyl acetate. The combined organic phases are dried over magnesium sulfate and concentrated under reduced pressure. The resulting product is triturated in a boiling mixture of 10 mL of dichloromethane and 30 mL of isopropyl ether and then filtered while hot. After drying, 0.31 g of the expected product is collected in the form of a beige-coloured solid.

m.p.: 247-249° C.

$^1$H NMR (DMSO-D$_6$), δ ppm: 10.6 (s, 1H); 9.3 (s, 1H); 7.9 (s, 1H); 7.6 (m, 2H); 7.5 (m, 2H); 7.35 (m, 2H); 7.2 (m, 1H); 7.1 (m, 1H); 6.9 (m, 2H); 5.9 (s, 2H); 5.1 (t, 1H); 4.6 (d, 2H).

LC-MS: 433 ([M+H]+, Rt=4.12 min.).

EXAMPLE 4

Compound 4

N-(3-Methyl-2-phenylimidazo[1,2-a]pyrid-6-yl)-5-fluoro-1-[(3-fluorophenyl)methyl]-1H-indole-2-carboxamide 4.1 N-[6-(Acetylamino)pyrid-3-yl]-5-fluoro-1-[(3-fluorophenyl)methyl]-1H-indole-2-carboxamide To a solution, stirred at 20° C. under an inert atmosphere, of 2 g (6.96 mmol) of 5-fluoro-1-[(3-fluorophenyl)methyl]-1H-indole-2-carboxylic acid, prepared according to the protocol described in step 1.1, in 40 mL of DMF are added 1.72 g (8.35 mmol) of dicyclohexylcarbodiimide (DCC) and 1.13 g (8.35 mmol) of 1-hydroxybenzotriazole hydrate (HOBT). The reaction mixture is stirred at room temperature for 30 minutes. 2.1 g (13.92 mmol) of 2-acetamido-5-aminopyridine and 20 mg of dimethylaminopyridine (DMAP) are then added to the reaction mixture. After stirring for 24 hours at 20° C., the reaction mixture is concentrated to dryness. The residue obtained is taken up in a mixture of 200 mL of saturated aqueous NaHCO$_3$ solution and 200 mL of ethyl acetate. The phases are separated by settling and the aqueous phase is extracted with 200 mL of ethyl acetate. The combined organic phases are dried over sodium sulfate and then concentrated under reduced pressure. A solid is collected, and is purified by chromatography on a column of silica, eluting with a mixture of dichloromethane and methanol. 2.6 g of the expected product are thus obtained.

$^1$H NMR (DMSO-D$_6$), δ ppm: 10.6 (s, 1H); 10.5 (s, 1H); 8.7 (s, 1H); 8.1 (s, 2H); 7.6 (m, 2H); 7.45 (s, 1H); 7.35 (m, 1H); 7.2 (m, 1H); 7.1 (m, 1H); 6.9 (m, 2H); 5.9 (s, 2H); 2.1 (s, 3H).

LC-MS: 421 ([M+H]+, Rt=1.10 min.).

4.2 N-[6-Aminopyrid-3-yl]-5-fluoro-1-[(3-fluorophenyl)methyl]-1H-indole-2-carboxamide To a suspension of 0.6 g (1.43 mmol) of N-[6-(acetylamino)pyrid-3-yl]-5-fluoro-1-[(3-fluorophenyl)methyl]-1H-indole-2-carboxamide, prepared according to the protocol described in step 4.1, in 9 mL of anhydrous methanol, stirred at 0° C. under an inert atmosphere, are added dropwise 2.03 mL (28.54 mmol) of acetyl chloride. The reaction mixture is stirred at 0° C. for 30 minutes and then gradually brought to 70° C. and stirred for 48 hours. The reaction mixture is concentrated to dryness. The residue obtained is taken up in a mixture of 200 mL of saturated aqueous NaHCO$_3$ solution and 200 mL of ethyl acetate. The phases are separated by settling and the aqueous phase is extracted with 200 mL of ethyl acetate. The combined organic phases are dried over sodium sulfate and then concentrated under reduced pressure. 0.46 g of the expected product is thus obtained.

$^1$H NMR (DMSO-D$_6$), δ ppm: 8.2 (s, 1H); 7.7 (m, 1H); 7.6 (m, 2H); 7.35 (m, 2H); 7.2 (m, 1H); 7.1 (m, 1H); 6.9 (m, 2H); 6.5 (d, 1H); 5.9 (s, 2H); 5.8 (s, 2H).

4.3 N-(3-Methyl-2-phenylimidazo[1,2-a]pyrid-6-yl)-5-fluoro-1-[(3-fluorophenyl)-methyl]-1H-indole-2-carboxamide (compound 4)

0.05 g (0.13 mmol) of N-[6-aminopyrid-3-yl]-5-fluoro-1-[(3-fluorophenyl)methyl]-1H-indole-2-carboxamide prepared according to the protocol described in step 4.2, 0.056 g (0.26 mmol) of 2-bromo-1-phenylpropan-1-one and 4 mL of acetonitrile are introduced into a 10 mL screw-topped tube equipped with a magnetic bar. The top is then screwed on and the tube is heated at 80° C. with stirring for 24 hours. After this time and cooling to room temperature, the precipitate obtained is filtered off and rinsed successively with 2 mL of acetonitrile and 2 mL of isopropyl ether. The solid obtained is dried under reduced pressure. 0.024 g of the expected product is thus obtained.

m.p.: 258-259° C.

$^1$H NMR (DMSO-D$_6$), δ ppm: 10.65 (s, 1H); 9.0 (s, 1H); 7.85 (d, 2H); 7.6 (m, 3H); 7.5 (m, 4H); 7.35 (m, 2H); 7.2 (m, 1H); 7.1 (m, 1H); 6.9 (m, 2H); 5.9 (s, 2H); 2.65 (s, 3H).

EXAMPLE 5

Compound 5

N-(2-Ethylimidazo[1,2-a]pyrid-6-yl)-5-fluoro-1-[(3-fluorophenyl)methyl]-1H-indole-2-carboxamide Compound 5 was prepared according to a process similar to that described in step 4.3, by reacting 0.1 g (0.26 mmol) of N-[6-aminopyrid-3-yl]-5-fluoro-1-[(3-fluorophenyl)-methyl]-1H-indole-2-carboxamide, prepared according to the protocol described in step 4.2, with 0.08 g (0.53 mmol) of 1-bromobutan-2-one in 4 mL of acetonitrile. 0.112 g of the expected product is thus obtained.

m.p.=278-279° C.

$^1$H NMR (DMSO D$_6$), δ (ppm): 9.65 (s, 1H); 8.25 (s, 1H); 8.05 (d, 1H); 7.95 (d, 1H); 7.65 (m, 2H); 7.55 (s, 1H); 7.35 (m, 1H); 7.25 (m, 1H); 7.1 (m, 1H); 6.9 (m, 2H); 5.9 (s, 2H); 2.9 (q, 2H); 1.3 (t, 3H).

LC-MS: 431 ([M+H]+, Rt=1.09 min.).

EXAMPLE 6

Compound 6

N-[2-(Thien-2-yl)imidazo[1,2-a]pyrid-6-yl]-5-fluoro-1-[(3-fluorophenyl)methyl]-1H-indole-2-carboxamide Compound 6 was prepared according to a process similar to that described in step 4.3, by reacting 0.1 g (0.26 mmol) of N-[6-aminopyrid-3-yl]-5-fluoro-1-[(3-fluorophenyl)-methyl]-1H-indole-2-carboxamide, prepared according to the protocol described in step 4.2, with 0.11 g (0.53 mmol) of 2-bromo-1-(thien-2-yl)ethanone in 4 mL of acetonitrile. 0.126 g of the expected product is thus obtained in the form of a white solid.

m.p.=316-318° C.

$^1$H NMR (DMSO D$_6$), δ (ppm): 10.8 (s, 1H); 9.5 (s, 1H); 8.6 (s, 1H); 7.8 (s, 2H); 7.7 (d, 1H); 7.6 (m, 3H); 7.55 (s, 1H); 7.35 (m, 1H); 7.2 (m, 2H); 7.1 (m, 1H); 6.95 (m, 2H); 5.9 (s, 2H).

LC-MS: 485 ([M+H]+, Rt=1.16 min.).

EXAMPLE 7

Compound 7

N-(2-tert-Butylimidazo[1,2-a]pyrid-6-yl)-5-fluoro-1-[(3-fluorophenyl)methyl]-1H-indole-2-carboxamide Compound 7 was prepared according to a process similar to that described in step 4.3, by reacting 0.1 g (0.26 mmol) of N-[6-aminopyrid-3-yl]-5-fluoro-1-[(3-fluorophenyl)-methyl]-1H-indole-2-carboxamide, prepared according to the protocol described in step 4.2, with 0.096 g (0.53 mmol) of 1-bromo-3,3-dimethylbutan-2-one in 4 mL of acetonitrile. 0.119 g of the expected product is thus obtained in the form of a white solid.

m.p.=190-192° C.

$^1$H NMR (DMSO D$_6$), δ (ppm): 10.9 (s, 1H); 9.6 (s, 1H); 8.3 (s, 1H); 8.0 (m, 2H); 7.65 (m, 2H); 7.55 (s, 1H); 7.35 (m, 1H); 7.25 (m, 1H); 7.1 (m, 1H); 6.95 (m, 2H); 5.9 (s, 2H); 1.4 (s, 9H).

LC-MS: 459 ([M+H]+, Rt=1.17 min.).

EXAMPLE 8

Compound 8

N-(2-Methoxymethylimidazo[1,2-a]pyrid-7-yl)-5-fluoro-1-[(3-fluorophenyl)methyl]-1H-indole-2-carboxamide 8.1 Ethyl 7-bromoimidazo[1,2-a]pyridine-2-carboxylate (Compound IIIc)

0.6 g (3.47 mmol) of 2-amino-4-bromopyridine, 1.55 g (7.15 mmol) of ethyl bromopyruvate and 4 mL of acetonitrile are placed in a 20 mL screw-topped tube equipped with a magnetic bar. The top is then screwed on and the tube is stirred at room temperature for 1 hour, and then heated at 150° C. with stirring for 30 minutes. After this time and cooling to room temperature, the precipitate obtained is filtered off, rinsed with acetonitrile and dried. The filtrate is concentrated to dryness and then purified by chromatography on a column of silica gel, eluting with a mixture of dichloromethane and methanol. The solid obtained after evaporating off the solvent is dried under reduced pressure. 530 mg of the expected product are obtained in total.

$^1$H NMR (DMSO-D$_6$), δ ppm: 8.65 (s, 1H); 8.6 (d, 1H); 8.05 (s, 1H); 7.3 (m, 1H); 4.3 (q, 2H); 1.3 (t, 3H).

8.2 (7-Bromoimidazo[1,2-a]pyrid-2yl)methanol (Compound IIId)

To a suspension of 0.25 g (0.93 mmol) of ethyl 7-bromoimidazo[1,2-a]pyridine-2-carboxylate, prepared according to the protocol described in step 8.1, in 4 mL of anhydrous dichloromethane, stirred at −19° C. under an inert atmosphere, are added dropwise 2.09 mL (2.09 mmol) of a molar solution of DIBAL-H in toluene. The reaction mixture is stirred at −19° C. for 3 hours and then hydrolysed at −40° C. by successive addition of 0.1 mL of methanol, 0.1 mL of water and 10 mL of 5N HCl. The reaction mixture is then basified with aqueous sodium hydroxide solution (24%) and then extracted with three times 100 mL of dichloromethane. The combined organic phases are dried over sodium sulfate and then concentrated under reduced pressure. The crude reaction product is then purified by chromatography on a column of silica gel, eluting with a mixture of dichloromethane and methanol. 110 mg of the expected product are thus obtained.

$^1$H NMR (DMSO-D$_6$), δ ppm: 8.0 (d, 1H); 7.8 (s, 1H); 7.6 (s, 1H); 6.9 (m, 1H); 4.9 (s, 2H).

8.3 7-Bromo-2-chloromethylimidazo[1,2-a]pyridine (Compound (IIIe)

To a solution of 110 mg (0.48 mmol) of (7-bromoimidazo [1,2-a]pyrid-2yl)methanol, prepared according to the protocol described in step 8.2, in 8 mL of anhydrous dichloromethane, stirred at room temperature under an inert atmosphere, is added 0.03 mL (0.53 mmol) of thionyl chloride. The reaction mixture is stirred at room temperature for 4 hours, hydrolysed at 0° C. by successive addition of 3 mL of cold water and 5 mL of saturated aqueous NaHCO$_3$ solution and then extracted with three times 10 mL of dichloromethane. The combined organic phases are dried over sodium sulfate and then concentrated under reduced pressure. 80 mg of the expected product are obtained.

$^1$H NMR (CDCl$_3$), δ ppm: 7.9 (d, 1H); 7.7 (s, 1H); 7.6 (s, 1H); 6.85 (m, 1H); 4.7 (s, 2H).

8.4 7-Bromo-2-methoxymethylimidazo[1,2-a]pyridine (Compound (IIIf)

To a solution of 81 mg (0.33 mmol) of 7-bromo-2-chloromethylimidazo[1,2-a]pyridine, prepared according to the protocol described in step 8.3, in 3 mL of anhydrous methanol, stirred at room temperature under an inert atmosphere, are added 35 mg (0.99 mmol) of sodium methoxide. The reaction mixture is stirred at 100° C. for 4 hours. After this time, the reaction medium, cooled to room temperature, is concentrated under reduced pressure, diluted with 10 mL of chloroform and then washed with 10 mL of saturated aqueous NaCl solution. The crude reaction product obtained after evaporating off the solvent under reduced pressure is purified by chromatography on a column of silica gel, eluting with a mixture of dichloromethane and methanol. 27 mg of the expected product are thus obtained.

$^1$H NMR (CDCl$_3$), δ ppm: 7.9 (d, 1H); 7.75 (s, 1H); 7.5 (s, 1H); 6.85 (m, 1H); 4.6 (s, 2H); 3.4 (s, 3H).

8.5 N-(2-Methoxymethylimidazo[1,2-a]pyrid-7-yl)-5-fluoro-1-[(3-fluorophenyl)-methyl]-1H-indole-2-carboxamide (compound 8)

20 mg (0.09 mmol) of copper iodide, 40 mg (0.14 mmol) of 5-fluoro-1-[(3-fluorophenyl)-methyl]-1H-indole-2-carboxamide, prepared according to the protocol described in step 1.2, 27 mg (0.11 mmol) of 7-bromo-2-methoxymethylimidazo[1,2-a]pyridine, prepared according to the protocol described in step 8.3, 50 mg (0.36 mmol) of potassium carbonate and 3 mL of anhydrous dioxane are placed in a 10 mL pressure tube specific for microwave reactors. The suspension is degassed for a few minutes, and 0.01 mL (0.04 mmol) of trans-1,2-cyclohexanediamine is then added. The tube is then sealed and heated in the microwave reactor at 150° C. for two 1-hour cycles. After this time, the suspension cooled to room temperature is poured into 20 mL of water and then extracted with 2×30 mL of dichloromethane. The combined organic phases are dried over magnesium sulfate and concentrated under reduced pressure. The crude reaction product is then purified by chromatography on a column of silica gel, eluting with a mixture of dichloromethane and methanol. 45 mg of the expected product are thus obtained.

m.p.: 215-216° C.

$^1$H NMR (DMSO-D$_6$), δ ppm: 10.7 (s, 1H); 8.5 (d, 1H); 8.0 (s, 1H); 7.8 (s, 1H); 7.6 (m, 2H); 7.5 (s, 1H); 7.3 (m, 1H); 7.2 (m, 2H); 7.05 (m, 1H); 6.9 (m, 2H); 5.9 (s, 2H); 4.5 (s, 2H); 3.3 (s, 3H).

LC-MS: 445 ([M−H]−, Rt=4.3 min.).

EXAMPLE 9

Compound 9

N-[2-(Hydroxymethypimidazo[1,2-a]pyrid-7-yl]-5-fluoro-1-[(3-fluorophenyl)methyl]-1H-indole-2-carboxamide 9.1 N-[2-(Ethyloxycarbonyl)imidazo[1,2-a]pyrid-7-yl]-5-fluoro-1-[(3-fluorophenyl)-methyl]-1H-indole-2-carboxamide The compound is prepared according to a process similar to that described in step 4.3, by reacting 0.2 g (0.53 mmol) of N-[2-aminopyrid-4-yl]-5-fluoro-1-[(3-fluorophenyl)-methyl]-1H-indole-2-carboxamide, prepared according to the protocol described in step 10.1, with 0.21 g (1.06 mmol) of ethyl 3-bromo-2-oxopropionate in 8 mL of acetonitrile. 70 mg of the expected product are thus obtained.

LC-MS: 475 ([M+H]+, Rt=1.09 min.).

$^1$H NMR (DMSO D$_6$), δ (ppm): 10.75 (s, 1H); 8.5 (m, 2H); 7.9 (s, 1H); 7.65 (m, 2H); 7.5 (s, 1H); 7.35 (m, 2H); 7.2 (m, 1H); 7.1 (m, 1H); 6.9 (m, 2H); 5.9 (s, 2H); 4.3 (q, 2H); 1.3 (t, 3H).

9.2 N-[2-(Hydroxymethypimidazo[1,2-a]pyrid-7-yl]-5-fluoro-1-[(3-fluorophenyl)-methyl]-1H-indole-2-carboxamide (compound 9)

Compound 9 was prepared according to a process similar to that described in step 8.2, by reacting 0.465 g (0.98 mmol) of N-[2-(ethyloxycarbonyl)imidazo[1,2-a]pyrid-7-yl]-5-fluoro-1-[(3-fluorophenyl)methyl]-1H-indole-2-carboxamide, prepared according to the protocol described in step 9.1, with 2.21 mL (2.21 mmol) of a molar solution of DIBAL-H in toluene, in 4 mL of dichloromethane. 80 mg of the expected product are obtained.

m.p.=244-245° C.

$^1$H NMR (DMSO D$_6$), δ (ppm): 10.6 (s, 1H); 8.48 (d, 1H); 8.0 (s, 1H); 7.7 (s, 1H); 7.6 (m, 2H); 7.5 (s, 1H); 7.35 (m, 1H); 7.2 (m, 2H); 7.05 (m, 1H); 6.9 (m, 2H); 5.9 (s, 2H); 5.1 (t, 1H); 4.6 (d, 2H).

LC-MS: 433 ([M+H]+, Rt=1.06 min.).

EXAMPLE 10

Compound 10

N-(2-Methyl-3-phenylimidazo[1,2-a]pyrid-7-yl)-5-fluoro-1-[(3-fluorophenyl)methyl]-1H-indole-2-carboxamide 10.1 N-[2-aminopyrid-4-yl]-5-fluoro-1-[(3-fluorophenyl)methyl]-1H-indole-2-carboxamide 0.2 g (1.05 mmol) of copper iodide, 0.6 g (2.10 mmol) of 5-fluoro-1-[(3-fluorophenyl)-methyl]-1H-indole-2-carboxamide, prepared according to the protocol described in step 1.2, 0.4 g (2.31 mmol) of 2-amino-4-bromopyridine, 1.16 g (8.40 mmol) of potassium carbonate and 15 mL of anhydrous dioxane are placed in a 10 mL pressure tube specific for microwave reactors. The suspension is degassed for a few minutes and 0.14 mL (1.15 mmol) of trans-1,2-cyclohexanediamine is then added. The tube is then sealed and heated in the microwave reactor at 170° C. for two 1-hour cycles, After this time, the suspension cooled to room temperature is poured into 50 mL of water and then extracted with 2×75 mL of dichlororomethane. The combined organic phases are dried over magnesium sulfate and concentrated under reduced pressure. The crude reaction product is then purified by chromatography on a column of silica gel, eluting with a mixture of dichloromethane and methanol. 0.425 g of the expected product is thus obtained in the form of a beige-coloured solid.

m.p.: 217-218° C.

$^1$H NMR (DMSO-D$_6$), δ ppm: 10.4 (s, 1H); 7.8 (d, 1H); 7.6 (m, 2H); 7.45 (s, 1H); 7.35 (m, 1H); 7.2 (m, 1H); 7.1 (m, 2H); 6.9 (m, 2H); 6.8 (d, 1H); 5.9 (m, 4H).

LC-MS: 379 ([M+H]+, Rt=1.03 min.).

10.2 N-(2-Methyl-3-phenylimidazo[1,2-a]pyrid-7-yl)-5-fluoro-1-[(3-fluorophenyl)-methyl]-1H-indole-2-carboxamide (compound 10)

0.1 g (0.26 mmol) of N-[2-aminopyrid-4-yl]-5-fluoro-1-[(3-fluorophenyl)methyl]-1H-indole-2-carboxamide, prepared according to the protocol described in step 10.1, 0.11 g (0.53 mmol) of 2-bromo-1-phenylpropan-1-one and 4 mL of acetonitrile are placed in a 10 mL pressure tube specific for microwave reactors. The tube is then sealed and heated in the microwave reactor at 150° C. for two 1-hour cycles. After this time, the reaction mixture is concentrated under reduced pressure. The crude reaction product is then purified by chromatography on a column of silica gel, eluting with a mixture of dichloromethane and methanol. 0.03 g of the expected product is thus obtained in the form of a beige-coloured solid.

m.p.: 305-307° C.

¹H NMR (DMSO-D$_6$), δ ppm: 10.7 (s, 1H); 8.35 (d, 1H); 8.1 (s, 1H); 7.85 (d, 2H); 7.6 (m, 2H); 7.5 (m, 3H); 7.35 (m, 3H); 7.2 (m, 1H); 7.1 (m, 1H); 6.9 (m, 2H); 5.9 (s, 2H); 2.7 (s, 3H).
LC-MS: 493 ([M+H]+, Rt=1.17 min.).

EXAMPLE 11

Compound 11

N-[2-(Thien-2-yl)imidazo[1,2-a]pyrid-7-yl]-5-fluoro-1-[(3-fluorophenyl)methyl]-1H-indole-2-carboxamide Compound 11 was prepared according to a process similar to that described in step 10.2, by reacting 0.1 g (0.26 mmol) of N-[2-aminopyrid-4-yl]-5-fluoro-1-[(3-fluoro-phenyl)methyl]-1H-indole-2-carboxamide, prepared according to the protocol described in step 10.1, with 0.11 g (0.53 mmol) of 2-bromo-1-(thien-2-yl)ethanone in 4 mL of acetonitrile. 0.026 g of the expected product is thus obtained in the form of a beige-coloured solid.
m.p.: 259-260° C.
¹H NMR (DMSO-D$_6$), δ ppm: 10.7 (s, 1H); 8.5 (d, 1H); 8.2 (s, 1H); 8.0 (s, 1H); 7.6 (m, 2H); 7.5 (m, 3H); 7.3 (m, 2H); 7.2 (m, 1H); 7.15 (m, 1H); 7.05 (m, 1H); 6.95 (m, 2H); 5.9 (s, 2H).
LC-MS: 485 ([M+H]+, Rt=1.13 min).

EXAMPLE 12

Compound 12

N-(2-Ethylimidazo[1,2-a]pyrid-7-yl)-5-fluoro-1-[(3-fluorophenyl)methyl-1H-indole-2-carboxamide Compound 12 was prepared according to a process similar to that described in step 10.2, by reacting 0.1 g (0.26 mmol) of N-[2-aminopyrid-4-yl]-5-fluoro-1-[(3-fluoro-phenyl)methyl]-1H-indole-2-carboxamide, prepared according to the protocol described in step 10.1, with 0.08 g (0.53 mmol) of 1-bromobutan-2-one in 4 mL of acetonitrile. 66 mg of the expected product are thus obtained.
m.p.: 158-159° C.
¹H NMR (DMSO D$_6$), δ (ppm): 11.2 (s, 1H); 8.65 (d, 1H); 8.4 (s, 1H); 7.9 (s, 1H); 7.55 (m, 4H); 7.35 (m, 1H); 7.2 (m, 1H); 7.05 (m, 1H); 6.9 (d, 1H); 6.8 (d, 1H); 5.9 (s, 2H); 2.8 (q, 2H); 1.25 (t, 3H).
LC-MS: 431 ([M+H]+, Rt=1.08 min.).

EXAMPLE 13

Compound 13

N-(2-tert-Butyl imidazo[1,2-a]pyrid-7-yl)-5-fluoro-1-[(3-fluorophenyl)methyl-1H-indole-2-carboxamide Compound 13 was prepared according to a process similar to that described in step 10.2, by reacting 0.1 g (0.26 mmol) of N-[2-aminopyrid-4-yl]-5-fluoro-1-[(3-fluoro-phenyl)methyl]-1H-indole-2-carboxamide, prepared according to the protocol described in step 10.1, with 0.096 g (0.53 mmol) of 1-bromo-3,3-dimethylbutan-2-one in 4 mL of acetonitrile. 0.116 g of the expected product is thus obtained.
m.p.: 327-328° C.
¹H NMR (DMSO D$_6$), δ (ppm): 11.2 (s, 1H); 8.7 (d, 1H); 8.45 (s, 1H); 8.0 (s, 1H); 7.7 (m, 4H); 7.35 (m, 1H); 7.25 (m, 1H); 7.1 (m, 1H); 6.9 (m, 2H); 5.9 (s, 2H); 1.4 (s, 8H).
LC-MS: 459 ([M+H]+, Rt=1.14 min.).

EXAMPLE 14

Compound 14

N-(2,3-Dimethylimidazo[1,2-a]pyrid-7-yl)-5-trifluoromethyl-1-[(3-fluorophenyl)methyl]-1H-indole-2-carboxamide 14.1 Methyl 2,3-dimethylimidazo[1,2-a]pyrid-7-carboxylate (Compound (IIIb)

To a suspension of 5 g (32.86 mmol) of methyl 2-aminopyridine-4-carboxylate and 5.52 g (65.72 mmol) of sodium hydrogen carbonate in 250 ml of ethanol are added 12.4 g (82.15 mmol) of 3-bromo-2-butanone. The reaction mixture is stirred at reflux for 2 hours. A further 12.4 g (82.15 mmol) of 3-bromo-2-butanone are then added to the reaction mixture and refluxing is continued with stirring for 15 hours.
After cooling to room temperature, the solvent is evaporated off. The residue is diluted with 50 mL of water and then basified by adding saturated NaHCO$_3$ to pH 8-9. The precipitate formed is filtered off, rinsed several times with water and then dried. 4 g of the expected product are obtained in the form of a beige-coloured solid.
NMR (DMSO-D$_6$) δ ppm: 8.3 (d, 1H); 8.05 (s, 1H); 7.3 (dd, 1H); 3.9 (s, 3H); 2.5 (s, 3H); 2.35 (s, 3H).

14.2 2,3-Dimethylimidazo[1,2-a]pyrid-7-carboxylic acid

To a solution of 1.85 g (9.06 mmol) of methyl 2,3-dimethylimidazo[1,2-a]pyridine-7-carboxylate, obtained according to the protocol described in step 14.1, in 50 mL of methanol is added a solution of 0.77 g (13.59 mmol) of potassium hydroxide in 1.5 mL of water. The reaction mixture is maintained at 50° C. for 18 hours. After cooling to room temperature, the solution is cooled to 0° C. and the pH of the reaction medium is adjusted to pH 5 by dropwise addition of 6N HCl. The precipitate formed is filtered off and rinsed with water and then with ether to give the expected acid quantitatively.
LC-MS: 191 ([M+H]+, Rt=0.44 min.).

14.3 tert-Butyl N-[2,3-dimethylimidazo[1,2-a]pyrid-7-yl]carbamate

To a suspension of 1.7 g (8.94 mmol) of 2,3-dimethylimidazo[1,2-a]pyrid-7-carboxylic acid, obtained according to the protocol described in step 14.2, in 29 mL of tert-butanol are added 3.19 g (11.62 mmol) of diphenylphosphorylazide and 3.11 mL (22.34 mmol) of triethylamine. After heating for 4 hours at 90° C. and for 12 hours at 40° C., the reaction medium is concentrated to dryness and then diluted with 20 ml of water. The precipitate obtained is filtered off, rinsed several times with water and then dried. Purification by flash chromatography on silica gel, eluting with a gradient of from 1 to 5% of methanol in dichloromethane, gives 1.15 g of the expected product in the form of a yellow solid.
NMR (DMSO-D$_6$) δ ppm: 7.8 (d, 1H); 7.5-7.2 (m, 2H); 2.4 (2s, 6H); 1.6 (s, 9H).

14.4 2,3-Dimethylimidazo[1,2-a]pyrid-7-ylamine hydrochloride

To a solution of 1.15 g (4.40 mmol) of tert-butyl 2,3-dimethylimidazo[1,2-a]pyrid-7-yl)carbamate, obtained according to the protocol described in step 14.3, in 15 ml of dioxane are added 15.4 ml (61.61 mmol) of a 4N solution of HCl in dioxane. The reaction mixture is maintained at 55° C. for 4 hours. After cooling to room temperature, the reaction mixture is diluted with diethyl ether, with stirring. The precipitate formed is filtered off, rinsed with ether and then dried under reduced pressure. 0.9 g of the expected 2,3-dimethylimidazo[1,2-a]pyrid-7-ylamine hydrochloride is obtained.

NMR (DMSO-$D_6$) δ ppm: 13.2 (s, 1H); 8.2 (d, 1H); 6.8 (d, 1H); 6.55 (s, 1H); 2.3 (s, 3H); 2.25 (s, 3H).

14.5 N-(2,3-Dimethylimidazo[1,2-a]pyrid-7-yl)-5-trifluoromethyl-1-[(3-fluorophenyl)-methyl]-1H-indole-2-carboxamide (compound 14)

To a solution, stirred at 20° C. under an inert atmosphere, of 1 g (2.96 mmol) of 5-trifluoromethyl-1-[(3-fluorophenyl)methyl]-1H-indole-2-carboxylic acid (WO 2006/072736) in 70 mL of DMF are added 0.74 g (3.56 mmol) of dicyclohexylcarbodiimide (DCC) and 0.48 g (3.56 mmol) of 1-hydroxybenzotriazole hydrate (HOBT). The reaction mixture is stirred at room temperature for 30 minutes. 0.7 g (4.45 mmol) of 2,3-dimethylimidazo[1,2-a]pyrid-7-ylamine, obtained according to the protocol described in step 14.4, and 100 mg of dimethylaminopyridine (DMAP) are then added to the reaction mixture. After stirring for 12 hours at 50° C., the reaction mixture is concentrated to dryness. The residue obtained is taken up in a mixture of 50 mL of water and 50 mL of ethyl acetate. The phases are separated by settling and the aqueous phase is extracted with 200 mL of ethyl acetate. The combined organic phases are dried over sodium sulfate and then concentrated under reduced pressure. The product is isolated after successive purifications by chromatography on a column of silica, eluting with a mixture of dichloromethane and methanol. 50 mg of the expected product are thus obtained.

m.p.=280-281° C.

$^1$H NMR (DMSO-$D_6$), δ ppm: 10.75 (s, 1H); 8.25 (s, 1H); 8.15 (d, 1H); 7.95 (s, 1H); 7.8 (d, 1H); 7.6 (m, 2H); 7.3 (m, 2H); 7.1 (m, 1H); 6.9 (m, 2H); 5.95 (s, 2H); 2.4 (s, 3H); 2.3 (s, 3H).

LC-MS: 481 ([M+H]+, Rt=1.18 min.).

EXAMPLE 15

Compound 15

N-(2-Ethylimidazo[1,2-a]pyrid-7-yl)-5-trifluoromethyl-1-[(3-fluorophenyl)methyl]-1H-pyrrolo[2,3-b]pyridine-2-carboxamide 15.1 5-Trifluoromethyl-1-[(3-fluorophenyl)methyl]-1H-pyrrolo[2,3-b]pyridine-2-carboxamide To a suspension, stirred at 20° C., of 1.5 g (4.43 mmol) of 5-trifluoromethyl-1-[(3-fluoro-phenyl)methyl]-1H-pyrrolo[2,3-b]pyridine-2-carboxylic acid (WO 2008/093024) in 40 mL of dry toluene are added 3.2 mL (44.34 mmol) of thionyl chloride. The reaction mixture is stirred at reflux for 2 hours and then concentrated under reduced pressure. The resulting product is taken up in 20 mL of dichloromethane and this solution is poured dropwise into a solution of 5.81 mL (44.34 mmol) of 30% aqueous ammonia. The reaction mixture is stirred for 14 hours at 20° C. After this time, a solid is collected by filtration, and is triturated in 50 mL of diisopropyl ether. After filtering off and drying under reduced pressure, 1.5 g of the expected product are collected.

m.p.: 203-204° C.

$^1$H NMR (DMSO-$D_6$), δ ppm: 8.78 (d, 1H); 8.65 (d, 1H); 8.29 (broad peak, 1H); 7.62 (broad peak, 1H), 7.4 (s, 1H); 7.32 (m, 1H); 7.05 (m, 1H); 6.92 (m, 2H); 6.0 (s, 2H).

LC-MS: 338 ([M+H]+, Rt=1.20 min.).

15.2 N-[2-Aminopyrid-4-yl]-5-trifluoromethyl-1-[(3-fluorophenyl)methyl]-1H-pyrrolo-[2,3-b]pyridine-2-carboxamide 0.056 g (0.30 mmol) of copper iodide, 0.2 g (0.59 mmol) of 5-trifluoromethyl-1-[(3-fluorophenyl)methyl]-1H-pyrrolo [2,3-b]pyridine-2-carboxamide, prepared according to the protocol described in step 15.1, 0.11 g (0.65 mmol) of 2-amino-4-bromopyridine, 0.33 g (2.37 mmol) of potassium carbonate and 5 mL of anhydrous dioxane are placed in a 10 mL pressure tube specific for microwave reactors. The suspension is degassed for a few minutes and 0.04 mL (0.33 mmol) of trans-1,2-cyclohexanediamine is then added. The tube is then sealed and heated in the microwave reactor at 170° C. for 45 minutes. After this time, the suspension cooled to room temperature is poured into 30 mL of water and then extracted with 2×40 mL of dichloromethane. The combined organic phases are dried over magnesium sulfate and concentrated under reduced pressure. The crude reaction product is then purified by chromatography on a column of silica gel, eluting with a mixture of dichloromethane and methanol. 0.22 g of the expected product is thus obtained in the form of a white solid.

m.p.: 197-198° C.

$^1$H NMR (DMSO-$D_6$), δ ppm: 10.6 (s, 1H); 8.85 (s, 1H); 8.75 (s, 1H); 7.85 (d, 1H); 7.65 (s, 1H); 7.35 (m, 1H); 7.1 (m, 2H); 6.9 (m, 2H); 6.8 (m, 1H); 5.95 (s, 2H); 5.85 (s, 2H).

LC-MS: 430 ([M+H]+, Rt=1.08 min.).

15.3 N-(2-Ethyl imidazo[1,2-a]pyrid-7-yl)-5-trifluoromethyl-1-[(3-fluorophenyl)methyl]-1H-pyrrolo[2,3-b]pyridine-2-carboxamide (compound 15)

0.125 g (0.29 mmol) of N-[2-aminopyrid-4-yl]-5-trifluoromethyl-1-[(3-fluorophenyl)-methyl]-1H-pyrrolo[2,3-b] pyridine-2-carboxamide, prepared according to the protocol described in step 15.2, 0.088 g (0.58 mmol) of 1-bromobutan-2-one and 4 mL of acetonitrile are placed in a 10 mL pressure tube specific for microwave reactors. The tube is then sealed and heated in the microwave reactor at 150° C. for two 1-hour cycles. After this time, the reaction mixture is concentrated under reduced pressure. The crude reaction product is then purified by chromatography on a column of silica gel, eluting with a mixture of dichloromethane and methanol. 0.076 g of the expected product is thus obtained in the form of a yellow solid.

m.p.: 264-265° C.

$^1$H NMR (DMSO-$D_6$), δ ppm: 10.8 (s, 1H); 8.85 (s, 1H); 8.8 (s, 1H); 8.45 (d, 1H); 7.95 (s, 1H); 7.65 (m, 2H); 7.35 (m, 1H); 7.2 (d, 1H); 7.1 (m, 1H); 6.95 (m, 2H); 6.0 (s, 2H); 2.7 (q, 2H); 1.3 (t, 3H).

LC-MS: 482 ([M+H]+, Rt=4.75 min.).

EXAMPLE 16

Compound 16

N-(2,3-Dimethylimidazo[1,2-a]pyrid-7-yl)-5-trifluoromethyl-1-[(3-fluorophenyl)methyl]-1H-pyrrolo[2,3-b]pyridine-2-carboxamide Compound 16 was prepared according to a process similar to that described in step 15.3, by reacting 0.12 g (0.28 mmol)

of N-[2-aminopyrid-4-yl]-5-trifluoromethyl-1-[(3-fluorophenyl)methyl]-1H-pyrrolo[2,3-b]pyridine-2-carboxamide, prepared according to the protocol described in step 15.2, with 0.084 g (0.56 mmol) of 3-bromobutan-2-one in 5 mL of acetonitrile. 45 mg of the expected product are obtained.

m.p.=287-288° C.

$^1$H NMR (DMSO-D$_6$), δ ppm: 10.8 (s, 1H); 8.85 (s, 1H); 8.8 (s, 1H); 8.2 (d, 1H); 8.0 (s, 1H); 7.65 (m, 1H); 7.35 (m, 1H); 7.28 (m, 1H); 7.1 (m, 1H); 6.95 (m, 2H); 6.0 (s, 2H); 2.4 (s, 3H); 2.3 (s, 3H).

LC-MS: 482 ([M+H]+, Rt=1.13 min.).

EXAMPLE 17

Compound 17

N-[2-(Hydroxymethyl)imidazo[1,2-a]pyrid-7-yl]-5-trifluoromethyl-1-[(3-fluorophenyl)-methyl]-1H-indole-2-carboxamide 17.1 5-Trifluoromethyl-1-[(3-fluorophenyl)methyl]-1H-indole-2-carboxamide To a suspension, stirred at 20° C., of 8 g (23.72 mmol) of 5-trifluoromethyl-1-(3-fluorobenzyl)-1H-indole-2-carboxylic acid (WO 2006/072736), in 150 mL of dry toluene are added 17.3 mL (237.2 mmol) of thionyl chloride. The reaction mixture is stirred for 2 hours at reflux and then concentrated under reduced pressure. The resulting product is taken up in 25 mL of dichloromethane, and this solution is poured dropwise into 9.32 mL of 30% aqueous ammonia solution. The reaction mixture is stirred for 14 hours at 20° C. After this time, a solid is collected by filtration, and is triturated in 50 mL of pentane. After filtering off and drying under reduced pressure, 5.87 g of the expected product are collected.

$^1$H NMR (DMSO-D$_6$), δ ppm: 8.28 (broad peak, 1H); 8.13 (s, 1H); 7.77 (d, 1H); 7.6 (m, 2H); 7.41 (s, 1H); 7.32 (m, 1H); 7.05 (m, 1H); 6.9 (m, 2H); 6 (s, 2H).

17.2 N-[2-Aminopyrid-4-yl]-5-trifluoromethyl-1-[(3-fluorophenyl)methyl]-1H-indole-2-carboxamide 0.056 g (0.30 mmol) of copper iodide, 0.2 g (0.59 mmol) of 5-trifluoromethyl-1-[(3-fluorophenyl)methyl]-1H-indole-2-carboxamide, prepared according to the protocol described in step 17.1, 0.12 g (0.71 mmol) of 2-amino-4-bromopyridine, 0.33 g (2.38 mmol) of potassium carbonate and 4 mL of anhydrous dioxane are placed in a 10 mL pressure tube specific for microwave reactors. The suspension is degassed for a few minutes and 0.04 mL (0.3 mmol) of trans-1,2-cyclohexanediamine is then added. The tube is then sealed and heated in the microwave reactor at 170° C. for 45 minutes. After this time, the suspension cooled to room temperature is poured into 30 mL of water and then extracted with 2×40 mL of dichloromethane. The combined organic phases are dried over magnesium sulfate and concentrated under reduced pressure. The crude reaction product is then purified by chromatography on a column of silica gel, eluting with a mixture of dichloromethane and methanol. 0.186 g of the expected product is thus obtained.

m.p.: 225-226° C.

$^1$H NMR (DMSO-D$_6$), δ ppm: 10.6 (s, 1H); 8.25 (s, 1H); 7.8 (m, 2H); 7.6 (m, 2H); 7.35 (m, 1H); 7.1 (m, 1H); 6.9 (m, 2H); 6.8 (d, 1H); 5.9 (s, 1H); 5.85 (s, 2H).

LC-MS: 429 ([M+H]+, Rt=4.55 min.).

17.3 N-[2-(Ethyloxycarbonyl)imidazo[1,2-a]pyrid-7-yl]-5-trifluoromethyl-1-[(3-fluoro-phenyl)methyl]-1H-indole-2-carboxamide The compound is prepared according to a process similar to that described in step 15.3, by reacting 0.23 g (0.54 mmol) of N-[2-aminopyrid-4-yl]-5-trifluoromethyl-1-[(3-fluorophenyl)methyl]-1H-indole-2-carboxamide, prepared according to the protocol described in step 17.2, with 0.21 g (1.07 mmol) of ethyl 3-bromo-2-oxopropionate in 4 mL of acetonitrile. 192 mg of the expected product are obtained.

m.p.=282-283° C.

$^1$H NMR (DMSO D$_6$), δ (ppm): 10.9 (s, 1H); 8.55 (d, 1H); 8.45 (s, 1H); 8.25 (s, 1H); 8.1 (s, 1H); 7.85 (d, 1H); 7.65 (s, 1H); 7.6 (d, 1H); 7.35 (m, 2H); 7.1 (m, 1H); 6.95 (d, 2H); 6.0 (s, 2H); 4.3 (q, 2H); 1.3 (t, 3H).

LC-MS: 525 ([M+H]+, Rt=4.83 min.).

17.4 N-[2-(Hydroxymethyl)imidazo[1,2-a]pyrid-7-yl]-5-trifluoromethyl-1-[(3-fluoro-phenyl)methyl]-1H-indole-2-carboxamide (compound 17)

To 0.47 mL (0.47 mmol) of a molar solution of LiAlH$_4$ diluted in 1 mL of anhydrous THF, cooled to −5° C., is added dropwise by syringe a suspension of 190 mg (0.36 mmol) of N-[2-(ethyloxycarbonyl)imidazo[1,2-a]pyrid-7-yl]-5-trifluoromethyl-1-[(3-fluorophenyl)-methyl]-1H-indole-2-carboxamide, prepared according to the protocol described in step 17.3, in 4 mL of anhydrous THF. After stirring for 3 hours at room temperature, the reaction medium is poured slowly into a mixture (v/v) of water and concentrated sodium hydroxide, and is then extracted with 3×100 mL of dichloromethane. The combined organic phases are dried over magnesium sulfate and then concentrated under reduced pressure. The crude reaction product obtained is purified by chromatography on a column of silica, eluting with a mixture of dichloromethane and methanol. 30 mg of the expected product are thus obtained.

m.p.=254-255° C.

$^1$H NMR (DMSO-D$_6$), δ ppm: 10.8 (s, 1H); 8.49 (d, 1H); 8.25 (s, 1H); 8.0 (s, 1H); 7.8 (d, 1H); 7.7 (s, 2H); 7.6 (m, 2H); 7.3 (m, 1H); 7.2 (m, 1H); 7.05 (m, 1H); 6.95 (d, 2H); 5.95 (s, 2H); 5.1 (m, 1H); 4.55 (d, 2H).

LC-MS: 483 ([M+H]+, Rt=1.29 min.).

EXAMPLE 18

Compound 18

N-[2-(Hydroxymethyl)imidazo[1,2-a]pyrid-7-yl]-5-trifluoromethyl-1-[(3-fluorophenyl)-methyl]-1H-pyrrolo[2,3-b]pyridine-2-carboxamide (Compound 18)

18.1 N-[2-(Ethyloxycarbonyl)imidazo[1,2-a]pyrid-7-yl]-5-trifluoromethyl-1-[(3-fluoro-phenyl)methyl]-1H-pyrrolo[2,3-b]pyridine-2-carboxamide The compound is prepared according to a process similar to that described in step 15.3, by reacting 0.197 g (0.46 mmol) of N-[2-aminopyrid-4-yl]-5-trifluoromethyl-1-[(3-fluorophenyl)methyl]-1H-pyrrolo[2,3-b]pyridine-2-carboxamide, prepared according to the protocol described in step 15.2, with 0.179 g (0.92 mmol) of ethyl 3-bromo-2-oxopropionate in 5 mL of acetonitrile. 130 mg of the expected product are obtained.

¹H NMR (DMSO-D₆), δ ppm: 10.9 (s, 1H); 8.9 (s, 1H); 8.8 (s, 1H); 8.5 (m, 2H); 8.1 (s, 1H); 7.7 (s, 1H); 7.35 (m, 2H); 7.1 (m, 1H); 6.95 (m, 2H); 6.0 (s, 2H); 4.3 (q, 2H); 1.3 (t, 3H).

18.2 N-[2-(Hydroxymethyl)imidazo[1,2-a]pyrid-7-yl]-5-trifluoromethyl-1-[(3-fluoro-phenyl)methyl]-1H-pyrrolo[2,3-b]pyridine-2-carboxamide (Compound 18)

Compound 18 was prepared according to a process similar to that described in step 17.4, by reacting 0.13 g (0.25 mmol) of N-[2-(ethyloxycarbonyl)imidazo[1,2-a]pyrid-7-yl]-5-trifluoromethyl-1-[(3-fluorophenyl)methyl]-1H-pyrrolo[2,3-b]pyridine-2-carboxamide, prepared according to the protocol described in step 18.1, with 0.32 mL of a molar solution of LiAlH₄ in 4 mL of tetrahydrofuran. 22 mg of the expected product are obtained.

m.p.=238-240° C.
¹H NMR (DMSO-D₆), δ ppm: 10.8 (s, 1H); 8.85 (s, 1H); 8.8 (s, 1H); 8.45 (d, 1H); 8.0 (s, 1H); 7.7 (s, 1H); 7.65 (s, 1H); 7.35 (m, 1H); 7.2 (m, 1H); 7.05 (m, 1H); 6.95 (m, 2H); 6.0 (s, 2H); 5.15 (t, 1H); 4.55 (d, 2H).
LC-MS: 484 ([M+H]+, Rt=1.13 min.).

EXAMPLE 19

Compound 19

N-(2-Methylimidazo[1,2-a]pyrid-7-yl)-5-fluoro-1-[(3-fluorophenyl)methyl]-1H-indole-2-carboxamide Compound 19 was prepared according to a process similar to that described in step 10.2, by reacting 0.12 g (0.32 mmol) of N-[2-aminopyrid-4-yl]-5-fluoro-1-[(3-fluoro-phenyl)methyl]-1H-indole-2-carboxamide, prepared according to the protocol described in step 10.1, with 0.059 g (0.63 mmol) of 1-chloropropan-2-one in 4 mL of acetonitrile. 50 mg of the expected product are thus obtained.

m.p.: 267-268° C.
¹H NMR (DMSO D₆), δ (ppm): 10.6 (s, 1H); 8.4 (d, 1H); 7.95 (s, 1H); 7.6 (m, 3H); 7.45 (s, 1H); 7.35 (m, 1H); 7.2 (m, 2H); 7.05 (m, 1H); 6.9 (m, 2H); 5.9 (s, 2H); 2.3 (s, 3H).
LC-MS: 417 ([M+H]+, Rt=1.2 min.).

EXAMPLE 20

Compound 20

N-(2-Methylpyrazolo[1,5-a]pyrimidin-6-yl)-5-fluoro-1-[(3-fluorophenyl)methyl]-1H-indole-2-carboxamide 80 mg (0.42 mmol) of copper iodide, 0.4 g (1.40 mmol) of 5-fluoro-1-[(3-fluorophenyl)-methyl]-1H-indole-2-carboxamide, obtained according to the protocol described in step 1.2, 0.32 g (1.54 mmol) of 6-bromo-2-methylpyrazolo[1,5-a]pyrimidine (WO 2006/128693), 0.38 g (2.79 mmol) of potassium carbonate and 10 mL of dioxane are mixed together in a pressure tube, under an inert atmosphere at 20° C. The suspension is degassed for a few minutes, 0.053 g (0.46 mmol) of trans-1,2-cyclohexanediamine is added and the tube is closed. The reaction mixture is stirred for 15 hours at 110° C. After this time, the suspension cooled to room temperature is poured into 50 mL of water and 50 mL of ethyl acetate. The aqueous phase is extracted with 2×30 mL of ethyl acetate. The combined organic phases are dried over magnesium sulfate and concentrated under reduced pressure. The resulting product is triturated in a boiling mixture of 5 mL of dichloromethane and 20 mL of isopropyl ether, and then filtered while hot. The solid obtained is purified by chromatography on a column of silica, eluting with a mixture of n-heptane and ethyl acetate. After drying, 0.23 g of the expected product is collected in the form of a white solid.

m.p.: 267-268° C.
¹H NMR (DMSO-D₆), δ ppm: 10.8 (s, 1H); 9.4 (s, 1H); 8.7 (s, 1H); 7.65 (m, 2H); 7.5 (s, 1H); 7.35 (m, 1H); 7.2 (m, 1H); 7.05 (m, 1H); 6.95 (m, 2H); 6.55 (s, 1H); 5.9 (s, 2H); 2.4 (s, 3H).
LC-MS: 418 ([M+H]+, Rt=1.26 min.).

EXAMPLE 21

Compound 21

N-[2-(Ethyloxycarbonyl)imidazo[1,2-b]pyridazin-6-yl]-5-fluoro-1-[(3-fluorophenyl)-methyl]-1H-indole-2-carboxamide

21.1 Ethyl 6-bromoimidazo[1,2-b]pyridazine-2-carboxylate

To a solution of 2.0 g (11.49 mmol) of 3-amino-5-bromopyridazine in 200 mL of absolute ethanol are added slowly 2.73 g (1.77 mmol) of ethyl 3-bromo-2-oxopropionate. The reaction mixture is refluxed for 18 hours.

After this time, the reaction mixture is cooled to room temperature and the precipitate formed is filtered off, rinsed with a minimum amount of ethanol and then oven-dried under reduced pressure. 1.33 g of the expected product are obtained.

¹H NMR (DMSO-D₆), δ ppm: 8.9 (s, 1H); 8.2 (d, 1H); 7.55 (d, 1H); 4.3 (q, 2H); 1.3 (t, 3H).
LC-MS: 270 ([M+H]+, Rt=0.88 min.).

21.2 N-[2-(Ethyloxycarbonyl)imidazo[1,2-b]pyridazin-6-yl]-5-fluoro-1-[(3-fluoro-phenyl)methyl]-1H-indole-2-carboxamide (compound 21)

Compound 21 was prepared according to a process similar to that described in Example 20, by reacting 0.4 g (1.40 mmol) of 5-fluoro-1-[(3-fluorophenyl)methyl]-1H-indole-2-carboxamide, prepared according to the protocol described in step 1.2, with 0.41 g (1.54 mmol) of ethyl 6-bromoimidazo [1,2-b]pyridazine-2-carboxylate, prepared according to the protocol described in step 21.1, in the presence of 80 mg (0.42 mmol) of copper iodide, 0.38 g (2.79 mmol) of potassium carbonate and 53 mg (0.46 mmol) of trans-1,2-cyclohexanediamine in 10 mL of dioxane. 20 mg of the expected product are thus obtained.

m.p.: 267-268° C.
¹H NMR (DMSO-D₆), δ ppm: 11.6 (s, 1H); 8.7 (s, 1H); 8.2 (d, 1H); 7.9 (d, 1H); 7.65 (m, 3H); 7.35 (m, 1H); 7.25 (m, 1H); 7.05 (m, 1H); 6.9 (m, 2H); 5.9 (s, 2H); 4.35 (q, 2H); 1.3 (t, 3H).
LC-MS: 476 ([M+H]+, Rt=1.26 min.).

EXAMPLE 22

Compound 22

N-[2-(Ethyloxycarbonyl)imidazo[1,2-a]pyrid-6-yl]-5-fluoro-1-[(3-fluorophenyl)methyl]-1H-indole-2-carboxamide Compound 22 was prepared according to a process similar to that described in step 4.3, by reacting 0.1 g (0.26 mmol) of N-[6-aminopyrid-3-yl]-5-fluoro-1-[(3-fluorophenyl)-methyl]-1H-indole-2-carboxamide, prepared according to the protocol described in step 4.2, with 0.105 g (0.53 mmol) of ethyl 3-bromo-2-oxopropionate in 4 mL of acetonitrile. 0.05 g of the expected product is obtained in the form of a white solid.

m.p.=242-245° C.

$^1$H NMR (DMSO D$_6$), δ (ppm): 10.8 (s, 1H); 10.55 (s, 1H); 8.8 (s, 1H); 7.8 (m, 2H); 7.65 (m, 2H); 7.55 (s, 1H); 7.35 (m, 1H); 7.2 (m, 1H); 7.05 (m, 1H); 6.9 (m, 2H); 5.9 (s, 2H); 4.4 (q, 2H); 1.35 (t, 3H).

LC-MS: 475 ([M+H]+, Rt=1.15 min.).

EXAMPLE 23

Compound 23

N-(2-Methylimidazo[1,2-a]pyrid-6-yl)-5-fluoro-1-[(3-fluorophenyl)methyl]-1H-indole-2-carboxamide 0.085 g (0.22 mmol) of N-[6-aminopyrid-3-yl]-5-fluoro-14[(3-fluorophenyl)methyl]-1H-indole-2-carboxamide, prepared according to the protocol described in step 4.2, and 0.043 g (0.45 mmol) of 1-chloropropan-2-one in 6 mL of acetonitrile are placed in a 10 mL pressure tube specific for microwave reactors. The tube is then sealed and heated in the microwave reactor at 150° C. for two 1-hour cycles. After this time, the reaction mixture is concentrated to dryness. The crude reaction product is then purified by chromatography on a column of silica gel, eluting with a mixture of dichloromethane and methanol. 0.058 g of the expected product is thus obtained in the form of a white solid.

m.p.: 200-203° C.

$^1$H NMR (DMSO-D$_6$), δ ppm: 10.5 (s, 1H); 9.2 (s, 1H); 7.8 (s, 1H); 7.6 (m, 2H); 7.45 (m, 2H); 7.35 (m, 2H); 7.2 (m, 1H); 7.1 (m, 1H); 6.9 (m, 2H); 5.9 (s, 2H); 2.3 (s, 3H).

LC-MS: 417 ([M+H]+, Rt=1.05 min.).

EXAMPLE 24

Compound 24

N-([1,2,4]Triazolo[1,5-a]pyrid-6-yl)-5-fluoro-14[(3-fluorophenyl)methyl]-1H-indole-2-carboxamide Compound 24 was prepared according to a process similar to that described in Example 20, by reacting 0.5 g (1.75 mmol) of 5-fluoro-1-[(3-fluorophenyl)methyl]-1H-indole-2-carboxamide, prepared according to the protocol described in step 1.2, with 0.35 g (1.75 mmol) of 6-bromo[1,2,4]triazolo[1,5-a]pyridine, in the presence of 99 mg (0.52 mmol) of copper iodide, 0.48 g (3.49 mmol) of potassium carbonate and 66 mg (0.58 mmol) of trans-1,2-cyclohexanediamine in 15 mL of dioxane. 393 mg of the expected product are thus obtained.

m.p.: 227-229° C.

$^1$H NMR (DMSO-D$_6$), δ ppm: 10.8 (s, 1H); 9.55 (s, 1H); 8.5 (s, 1H); 7.9 (s, 2H); 7.60 (m, 2H); 7.5 (s, 1H); 7.35 (m, 1H); 7.20 (m, 1H); 7.05 (m, 1H); 6.9 (m, 2H); 5.9 (s, 2H)

LC-MS: 404 ([M+H]+, Rt=1.16 min.).

Table 1 below illustrates the chemical structures and the physical properties of a number of compounds of general formula (I) according to the invention.

In this table:

the compounds of general formula (I) are defined with n equal to 1 and W=O;

the "m.p. (° C.)" column indicates the melting points of the products in degrees Celsius (° C.);

the compounds are in the form of the free base.

TABLE 1

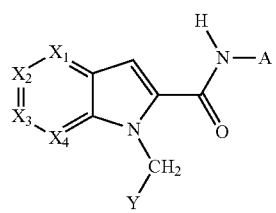

(I)

| No. | X$_1$, X$_2$, X$_3$, X$_4$ | Y | A | m.p. (° C.) |
|---|---|---|---|---|
| 1 | CH, C—F, CH, CH | 3-fluorophenyl | 2,3-dimethylimidazo[1,2-a]pyrid-7-yl | 251-253 |
| 2 | CH, C—F, CH, CH | 3-fluorophenyl | 2,3-dimethylimidazo[1,2-a]pyrid-6-yl | 220-242 |
| 3 | CH, C—F, CH, CH | 3-fluorophenyl | 2-hydroxymethylimidazo-[1,2-a]pyrid-6-yl | 247-249 |
| 4 | CH, C—F, CH, CH | 3-fluorophenyl | 3-methyl-2-phenylimidazo-[1,2-a]pyrid-6-yl | 258-259 |
| 5 | CH, C—F, CH, CH | 3-fluorophenyl | 2-ethylimidazo[1,2-a]pyrid-6-yl | 278-279 |
| 6 | CH, C—F, CH, CH | 3-fluorophenyl | 2-thien-2-ylimidazo[1,2-a]pyrid-6-yl | 316-318 |
| 7 | CH, C—F, CH, CH | 3-fluorophenyl | 2-tert-butylimidazo[1,2-a]pyrid-6-yl | 190-192 |
| 8 | CH, C—F, CH, CH | 3-fluorophenyl | 2-(methyloxymethyl)-imidazo-[1,2-a]pyrid-7-yl | 215-216 |
| 9 | CH, C—F, CH, CH | 3-fluorophenyl | 2-(hydroxymethyl)imidazo-[1,2-a]pyrid-7-yl | 244-245 |
| 10 | CH, C—F, CH, CH | 3-fluorophenyl | 2-methyl-3-phenylimidazo-[1,2-a]pyrid-7-yl | 305-307 |

TABLE 1-continued (I)

$$\text{Structure (I): fused bicyclic with } X_1, X_2, X_3, X_4 \text{ positions, pyrrole-N-CH}_2\text{-Y, and -C(=O)-NH-A substituent}$$

| No. | $X_1, X_2, X_3, X_4$ | Y | A | m.p. (°C.) |
|---|---|---|---|---|
| 11 | CH, C—F, CH, CH | 3-fluorophenyl | 2-thien-2-ylimidazo[1,2-a]pyrid-7-yl | 259-260 |
| 12 | CH, C—F, CH, CH | 3-fluorophenyl | 2-ethylimidazo[1,2-a]pyrid-7-yl | 158-159 |
| 13 | CH, C—F, CH, CH | 3-fluorophenyl | 2-tert-butylimidazo[1,2-a]pyrid-7-yl | 327-328 |
| 14 | CH, C—CF$_3$, CH, CH | 3-fluorophenyl | 2,3-dimethylimidazo[1,2-a]pyrid-7-yl | 280-281 |
| 15 | CH, C—CF$_3$, CH, N | 3-fluorophenyl | 2-ethylimidazo[1,2-a]pyrid-7-yl | 264-265 |
| 16 | CH, C—CF$_3$, CH, N | 3-fluorophenyl | 2,3-dimethylimidazo[1,2-a]pyrid-7-yl | 287-288 |
| 17 | CH, C—CF$_3$, CH, CH | 3-fluorophenyl | 2-(hydroxymethyl)imidazo[1,2-a]pyrid-7-yl | 254-255 |
| 18 | CH, C—CF$_3$, CH, N | 3-fluorophenyl | 2-(hydroxymethyl)imidazo[1,2-a]pyrid-7-yl | 238-240 |
| 19 | CH, C—F, CH, CH | 3-fluorophenyl | 2-methylimidazo[1,2-a]pyrid-7-yl | 267-268 |
| 20 | CH, C—F, CH, CH | 3-fluorophenyl | 2-methylpyrazolo[1,5-a]pyrimidin-6-yl | 267-268 |
| 21 | CH, C—F, CH, CH | 3-fluorophenyl | 2-ethyloxycarbonylimidazo[1,2-b]pyridazin-6-yl | 267-268 |
| 22 | CH, C—F, CH, CH | 3-fluorophenyl | 2-(ethyloxycarbonyl)imidazo[1,2-a]pyrid-6-yl | 242-245 |
| 23 | CH, C—F, CH, CH | 3-fluorophenyl | 2-methylimidazo[1,2-a]pyrid-6-yl | 200-203 |
| 24 | CH, C—F, CH, CH | 3-fluorophenyl | [1,2,4]triazolo[1,5-a]pyrid-6-yl | 227-229 |

The compounds according to the invention underwent in vitro and in vivo pharmacological tests that demonstrated their value as therapeutically active substances. These compounds have antagonist or agonist activity towards the TRPV1 (or VR1) receptors.

Test of Inhibition of the Current Induced with Capsaicin on Rat DRGs

Primary culture of rat dorsal root ganglion (DRG) cells:
DRG neurones naturally express the TRPV1 receptor.

The primary cultures of newborn rat DRGs are prepared using 1-day-old rats. Briefly, after dissection, the ganglions are trypsinized and the cells dissociated by mechanical trituration. The cells are resuspended in an Eagle basal culture medium containing 10% foetal calf serum, 25 mM KCl, 2 mM glutamine, 100 µg/ml gentamicin and 50 ng/ml of NGF, and then deposited on glass slides coated with laminin (0.25× $10^6$ cells per slide), which are then placed in Corning 12-well dishes. The cells are incubated at 37° C. in a humidified atmosphere containing 5% CO$_2$ and 95% air. Cytosine β-D-arabinoside (1 µM) is added 48 hours after culturing, to prevent the growth of non-neuronal cells. The slides are transferred into experimental chambers for the patch-clamp studies after 7-10 days of culturing.

Electrophysiology:

The measuring chambers (volume 800 µl) containing the cell preparation are placed on the platform of an inverted microscope (Olympus IMT2) equipped with Hoffman optics (Modulation Contrast, New York) and observed at a magnification of 400×. The chambers are continuously gravity-influxed (2.5 ml/min) using a solution distributor accepting 8 inlets and whose sole outlet, consisting of a polyethylene tube (aperture 500 µm), is placed less than 3 mm from the cell under study. The "whole cell" configuration of the patch-clamp technique was used. The borosilicate-glass pipettes (resistance 5-10 MOhms) are brought to the cell by means of a 3D piezoelectric micromanipulator (Burleigh, PC1000). The overall currents (membrane potential set at −60 mV) are recorded with an Axopatch 1D amplifier (Axon Instruments, Foster City, Calif.), connected to a PC running the Pclamp8 software (Axon Instrument). The current plots are recorded on paper and simultaneously digitized (sampling frequency 15 to 25 Hz) and acquired on the hard drive of the PC.

The application of a 300 nM capsaicin solution induces on the DRG cells (voltage set at −70 mV) an entering cationic current. In order to minimize the desensitization of the receptors, a minimum interval of 1 minute between two applications of capsaicin is observed. After a control period (stabilization of the capsaicin response alone), the test compounds are applied alone at a given concentration (concentration of 10 nM or 1 nM) for a time of 4 to 5 minutes, during which several capsaicin+compound tests are performed (to obtain the maximum inhibition). The results are expressed as a percentage of inhibition of the control capsaicin response.

In the case of the VR1 antagonist compounds, the percentages of inhibition of the capsaicin response (1 µM) are between 20% and 100% for the most active compounds of the invention tested at concentrations of from 0.1 to 100 nM. They are therefore effective antagonists of receptors of TRPV1 type. Table 2 gives a few examples of the percentage of inhibition obtained with the compounds of the invention.

TABLE 2

| Compound No. | % inhibition in DRG patch |
|---|---|
| 1 | 81.5% (1 nM) |
| 20 | 80% (100 nM) |

The compounds of the invention may thus be used for the preparation of medicaments, especially for the preparation of a medicament for preventing or treating pathologies in which receptors of TRPV1 type are involved.

The compounds of the invention may be useful for preventing or treating pathologies in which receptors of TRPV1 type are involved.

Thus, a subject of the invention is medicaments comprising at least one compound of formula (I), or a pharmaceutically acceptable salt, or alternatively a hydrate or a solvate of the said compound.

These medicaments find their therapeutic use especially in the prevention and/or treatment of pain and inflammation, chronic pain, neuropathic pain (trauma-related, diabetic, metabolic, infection-related or toxic pain, or pain induced by an anticancer or iatrogenic treatment), (osteo)arthritic pain, rheumatic pain, fibromyalgia, back pain, cancer-related pain, facial neuralgia, headaches, migraine, dental pain, burns, sunburn, animal bites or insect bites, post-herpetic neuralgia, muscular pain, trapped nerves (central and/or peripheral), spinal column and/or brain trauma, ischaemia (of the spinal column and/or the brain), neurodegeneration, haemorrhagic strokes (of the spinal column and/or of the brain) and post-stroke pain.

The compounds of the invention may also be used for preventing and/or treating metabolic disorders such as diabetes.

The compounds of the invention may be used for preventing and/or treating urological disorders such as hyperactivity of the bladder, vesical hyperreflexia, vesical instability, incontinence, urgent micturition, urinary incontinence, cystitis, nephritic colic, pelvic hypersensitivity and pelvic pain.

The compounds of the invention may be useful for preventing and/or treating gynaecological disorders, for instance vulvodynia and pain associated with salpingitis or with dysmenorrhoea.

These products may also be used for preventing and/or treating gastrointestinal disorders such as gastro-oesophageal reflux disorder, stomach ulcers, duodenal ulcers, functional dyspepsia, colitis, IBS, Crohn's disease, pancreatitis, oesophagitis and biliary colic.

Similarly, the products of the present invention may be useful in the prevention and/or treatment of respiratory disorders such as asthma, coughing, chronic obstructive pulmonary disease (COPD), bronchoconstriction and inflammatory disorders of the respiratory system.

These products may also be used for preventing and/or treating psoriasis, pruritus, dermal, ocular or mucous irritation, herpes and zona.

The compounds of the invention may also be used for treating depression.

The compounds of the invention may also be used for treating central nervous system diseases such as multiple sclerosis.

The compounds of the invention may also be used for treating cancers.

According to another of its aspects, the present invention relates to pharmaceutical compositions comprising, as active principle, at least one compound according to the invention. These pharmaceutical compositions contain an effective dose of at least one compound according to the invention or a pharmaceutically acceptable salt, a hydrate or a solvate of the said compound and also at least one pharmaceutically acceptable excipient.

The said excipients are chosen, according to the pharmaceutical form and the desired mode of administration, from the usual excipients known to those skilled in the art.

The pharmaceutical compositions of the present invention may be administered via the oral, sublingual, subcutaneous, intramuscular, intravenous, topical, local, intratracheal, intranasal, transdermal or rectal route. These compositions may be administered in a unit administration form, as a mixture with standard pharmaceutical excipients. They are intended to be administered to animals and human beings for the prophylaxis or treatment of the disorders or diseases mentioned above.

The appropriate unit forms of administration include oral forms such as tablets, soft or hard gel capsules, powders, granules and oral solutions or suspensions, sublingual, buccal, intratracheal, intraocular and intranasal administration forms, forms for administration by inhalation, topical, transdermal, subcutaneous, intramuscular or intravenous administration forms, rectal administration forms and implants. For topical application, the compounds according to the invention may be used in creams, gels, pomades or lotions.

By way of example, a unit form of administration of a compound according to the invention in tablet form may comprise the following components:

| Compound according to the invention | 50.0 mg |
|---|---|
| Mannitol | 223.75 mg |
| Croscarmellose sodium | 6.0 mg |
| Corn starch | 15.0 mg |
| Hydroxypropylmethylcellulose | 2.25 mg |
| Magnesium stearate | 3.0 mg |

The said unit forms are dosed to allow a daily administration of from 0.001 to 30 mg of active principle per kg of body weight, according to the galenical form.

There may be particular cases in which higher or lower dosages are appropriate: such dosages do not depart from the scope of the invention. According to the usual practice, the dosage that is appropriate for each patient is determined by the doctor according to the mode of administration, the weight and the response of the said patient.

According to another of its aspects, the present invention also relates to a method for treating the pathologies indicated above, which comprises the administration to a patient of an effective dose of a compound according to the invention, or a pharmaceutically acceptable salt, or hydrate or solvate thereof.

What is claimed is:

1. A compound corresponding to formula (I):

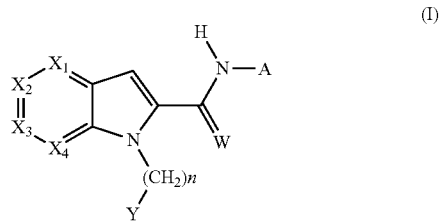

wherein:
X$_1$, X$_2$, X$_3$ and X$_4$ represent, independently of each other, a nitrogen atom or a group C—R$_1$; wherein when one from among X$_1$, X$_2$, X$_3$ and X$_4$ represents a nitrogen atom, the others correspond to a group C—R$_1$;

W represents an oxygen or sulfur atom;

n is equal to 0, 1, 2 or 3;

Y represents an aryl or a heteroaryl optionally substituted with one or more groups chosen from a halogen atom and a group C$_1$-C$_6$-alkyl, C$_3$-C$_7$-cycloalkyl, C$_3$-C$_7$-cycloalkyl-C$_1$-C$_3$-alkylene, C$_1$-C$_6$-fluoroalkyl, hydroxyl, C$_1$-C$_6$-alkoxy, C$_3$-C$_7$-cycloalkyloxy, C$_3$-C$_7$-cycloalkyl-C$_1$-C$_6$-alkylene-O—, C$_1$-C$_6$-fluoroalkoxy, cyano, C(O)NR$_3$R$_4$, nitro, NR$_3$R$_4$, C$_1$-C$_6$-thioalkyl, thiol, —S(O)—C$_1$-C$_6$-alkyl, —S(O)$_2$—C$_1$-C$_6$-alkyl, SO$_2$NR$_3$R$_4$, NR$_5$C(O)R$_6$; NR$_5$SO$_2$R$_7$, C(O)NR$_3$R$_4$, OC(O)NR$_3$R$_4$, —Si—(C$_1$-C$_6$-alkyl)$_3$, —SF$_5$, aryl-C$_1$-C$_5$-alkylene or aryl, heteroaryl-C$_1$-C$_5$-alkylene or heteroaryl; the groups C$_1$-C$_6$-alkyl, C$_3$-C$_7$-cycloalkyl, C$_3$-C$_7$-cycloalkyl-C$_1$-C$_3$-alkylene, C$_1$-C$_6$-fluoroalkyl, C$_1$-C$_6$-alkoxy, C$_3$-C$_7$-cycloalkyloxy and C$_3$-C$_7$-cycloalkyl-C$_1$-C$_6$-alkylene-O— being optionally substituted with a hydroxyl, C$_1$-C$_6$-alkoxy or NR$_3$R$_4$ group; the aryl and heteroaryl groups being optionally substituted with one or more substituents R$_8$, which may be identical to or different from each other;

A represents a bicyclic heteroaryl of formula:

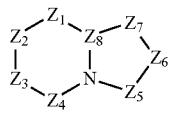

wherein:
Z$_1$, Z$_2$, Z$_3$ and Z$_4$ represent, independently of each other, a carbon atom, a nitrogen atom or a group C—R$_{2a}$;

Z$_5$, Z$_6$ and Z$_7$ represent, independently of each other, a nitrogen atom or a group C—R$_{2b}$;

Z$_8$ represents a carbon atom;

wherein three, at most, from among Z$_1$, Z$_2$, Z$_3$, Z$_4$, Z$_5$, Z$_6$ and Z$_7$ represent a nitrogen atom; one from among Z$_1$, Z$_2$, Z$_3$ and Z$_4$, corresponding to a carbon atom, being bonded to the nitrogen atom of the amide or thioamide of formula (I);

R$_1$ is chosen from a hydrogen atom, a halogen atom, C$_1$-C$_6$-alkyl, C$_3$-C$_7$-cycloalkyl, C$_3$-C$_7$-cycloalkyl-C$_1$-C$_3$-alkylene, C$_1$-C$_6$-fluoroalkyl, aryloxy-C$_1$-C$_6$-alkyl, heteroaryloxy-C$_1$-C$_6$-alkyl, aryl-C$_1$-C$_3$-alkylenoxy-C$_1$-C$_6$-alkyl, heteroaryl-C$_1$-C$_3$-alkylenoxy-C$_1$-C$_6$-alkyl, arylthio-C$_1$-C$_6$-alkyl, heteroarylthio-C$_1$-C$_6$-alkyl, aryl-C$_1$-C$_3$-alkylenethio-C$_1$-C$_6$-alkyl, heteroaryl-C$_1$-C$_3$-alkylenethio-C$_1$-C$_6$-alkyl, C$_1$-C$_6$-alkoxy, C$_3$-C$_7$-cycloalkyloxy, C$_3$-C$_7$-cycloalkyl-C$_1$-C$_3$-alkylenoxy, C$_1$-C$_6$-fluoroalkoxy, cyano, C(O)NR$_3$R$_4$, nitro, NR$_3$R$_4$, C$_1$-C$_6$-thioalkyl, C$_3$-C$_7$-cycloalkylthio, C$_3$-C$_7$-cycloalkyl-C$_1$-C$_3$-alkylenethio, —S(O)—C$_1$-C$_6$-alkyl, —S(O)—C$_3$-C$_7$-cycloalkyl, —S(O)—C$_1$-C$_3$-alkylene-C$_3$-C$_7$-cycloalkyl, C$_1$-C$_6$-alkyl-S(O)$_2$—, C$_1$-C$_6$-fluoroalkyl-S(O)$_2$—, C$_3$-C$_7$-cycloalkyl-S(O)$_2$—, C$_3$-C$_7$-cycloalkyl-C$_1$-C$_3$-alkylene-S(O)$_2$—, SO$_2$NR$_3$R$_4$, (C$_1$-C$_6$-alkyl)$_3$-Si—, —SF$_5$, NR$_5$C(O)R$_6$, NR$_5$SO$_2$R$_7$, C(O)NR$_3$R$_4$, OC(O)NR$_3$R$_4$, aryl, heteroaryl, aryl-C$_1$-C$_5$-alkylene, heteroaryl-C$_1$-C$_5$-alkylene, aryloxy, arylthio, heteroaryloxy or heteroarylthio; the heteroaryl or aryl groups being optionally substituted with one or more substituents R$_8$, which may be identical to or different from each other;

R$_{2a}$ represents a hydrogen atom, a halogen atom or a group C$_1$-C$_6$-alkyl, C$_3$-C$_7$-cycloalkyl, C$_3$-C$_7$-cycloalkyl-C$_1$-C$_3$-alkylene, C$_1$-C$_6$-fluoroalkyl, C$_1$-C$_6$-alkoxy, C$_3$-C$_7$-cycloalkyloxy, C$_3$-C$_7$-cycloalkyl-C$_1$-C$_3$-alkylene-O—, hydroxyl, thiol or C$_1$-C$_6$-fluoroalkoxy;

R$_{2b}$ represents a hydrogen atom, a halogen atom or a group C$_1$-C$_6$-alkyl, C$_3$-C$_7$-cycloalkyl, C$_3$-C$_7$-cycloalkyl-C$_1$-C$_3$-alkylene, C$_1$-C$_6$-fluoroalkyl, C$_1$-C$_6$-alkoxy, hydroxyl, thiol, oxo, thio, C$_3$-C$_7$-cycloalkyloxy, C$_1$-C$_6$-fluoroalkoxy, C$_3$-C$_7$-cycloalkyl-C$_1$-C$_3$-alkylenoxy, C$_1$-C$_6$-alkoxy-C$_1$-C$_3$-alkylene, C$_3$-C$_7$-cycloalkyloxy-C$_1$-C$_3$-alkylene, C$_3$-C$_7$-cycloalkyl-C$_1$-C$_3$-alkylenoxy-C$_1$-C$_3$-alkylene, C$_1$-C$_6$-alkyl-C(O)—O—C$_1$-C$_3$-alkylene, C$_1$-C$_6$-alkyl-C(O)—O—, C$_3$-C$_7$-cycloalkyl-C(O)—O—C$_1$-C$_3$-alkylene, C$_3$-C$_7$-cycloalkyl-C(O)—O—, C$_1$-C$_6$-fluoroalkyl-C(O)—O—C$_1$-C$_3$-alkylene, C$_1$-C$_6$-fluoroalkyl-C(O)—O—, C(O)NR$_3$R$_4$, C(O)O—C$_1$-C$_6$-alkyl, cyano, CHO, CO$_2$H, —C(O)—C$_1$-C$_6$-alkyl, —C(O)—C$_3$-C$_7$-cycloalkyl, phenyl or thienyl; the groups C$_1$-C$_6$-alkyl, C$_3$-C$_7$-cycloalkyl, C$_3$-C$_7$-cycloalkyl-C$_1$-C$_3$-alkylene, C$_1$-C$_6$-fluoroalkyl, C$_1$-C$_6$-alkoxy, C$_3$-C$_7$-cycloalkyloxy, C$_1$-C$_6$-fluoroalkoxy, C$_3$-C$_7$-cycloalkyl-C$_1$-C$_3$-alkylenoxy, C$_1$-C$_6$-alkoxy-C$_1$-C$_3$-alkylene, C$_3$-C$_7$-cycloalkyloxy-C$_1$-C$_3$-alkylene and C$_3$-C$_7$-cycloalkyl-C$_1$-C$_3$-alkylenoxy-C$_1$-C$_3$-alkylene optionally being substituted with a hydroxyl, C$_1$-C$_6$-alkoxy or NR$_3$R$_4$ group;

R$_3$ and R$_4$ represent, independently of each other, a hydrogen atom or a group C$_1$-C$_6$-alkyl, C$_3$-C$_7$-cycloalkyl, C$_3$-C$_7$-cycloalkyl-C$_1$-C$_3$-alkylene, aryl-C$_1$-C$_5$-alkylene or aryl, or R$_3$ and R$_4$ together form, with the nitrogen atom that bears them, an azetidine, pyrrolidine, piperidine, azepine, morpholine, thiomorpholine, piperazine or homopiperazine group; the group NR$_3$R$_4$ being optionally substituted with a group C$_1$-C$_6$-alkyl, C$_3$-C$_7$-cycloalkyl, C$_3$-C$_7$-cycloalkyl-C$_1$-C$_3$-alkylene, aryl-C$_1$-C$_6$-alkylene, aryl, heteroaryl, aryl-S(O)$_2$—, C$_1$-C$_6$-alkyl-S(O)$_2$—, C$_1$-C$_6$-fluoroalkyl-S(O)$_2$, C$_3$-C$_7$-cycloalkyl-S(O)$_2$—, C$_3$-C$_7$-cycloalkyl-C$_1$-C$_3$-alkylene-S(O)$_2$—, aryl-C(O)—, C$_1$-C$_6$-alkyl-C(O)—, C$_3$-C$_7$-cycloalkyl-C(O)—, C$_3$-C$_7$-cycloalkyl-C$_1$-C$_3$-alkylene-C(O)—, C$_1$-C$_6$-fluoroalkyl-C(O)—, hydroxyl, C$_1$-C$_6$-alkyloxy, C$_3$-C$_7$-cycloalkyloxy, C$_3$-C$_7$-cycloalkyl-C$_1$-C$_3$-alkylenoxy, C$_1$-C$_6$-fluoroalkyl, aryloxy-C$_1$-C$_6$-alkylene, aryloxy, heteroaryloxy-C$_1$-C$_6$-alkylene or heteroaryloxy;

R$_5$ and R$_6$ represent, independently of each other, a hydrogen atom or a group C$_1$-C$_6$-alkyl, C$_3$-C$_7$-cycloalkyl, C$_3$-C$_7$-cycloalkyl-C$_1$-C$_3$-alkylene, aryl-C$_1$-C$_6$-alkylene or aryl; the aryl group being optionally substituted with one or more substituents chosen from a halogen atom and a group C$_1$-C$_6$-alkyl, C$_3$-C$_7$-cycloalkyl, C$_3$-C$_7$-cycloalkyl-C$_1$-C$_3$-alkylene, C$_1$-C$_6$-fluoroalkyl, C$_1$-C$_6$-alkoxy, C$_3$-C$_7$-cycloalkyloxy, C$_3$-C$_7$-cycloalkyl-C$_1$-C$_3$-alkylenoxy, C$_1$-C$_6$-fluoroalkoxy, nitro or cyano;

or R$_5$ and R$_6$ together form a 4- to 7-membered lactam comprising the nitrogen atom and the C(O) group that bear them;

R$_7$ represents a group C$_1$-C$_6$-alkyl, C$_3$-C$_7$-cycloalkyl, C$_3$-C$_7$-cycloalkyl-C$_1$-C$_3$-alkylene, aryl-C$_1$-C$_6$-alkylene or aryl; the aryl group being optionally substituted with one or more substituents chosen from a halogen atom and a group C$_1$-C$_6$-alkyl, C$_3$-C$_7$-cycloalkyl, C$_3$-C$_7$-cycloalkyl-C$_1$-C$_3$-alkylene, C$_1$-C$_6$-fluoroalkyl, C$_1$-C$_6$- alkoxy, $C_3$-$C_7$-cycloalkyloxy, $C_3$-$C_7$-cycloalkyl-$C_1$-$C_3$-alkylenoxy, $C_1$-$C_6$-fluoroalkoxy, nitro or cyano;

or $R_5$ and $R_7$ together form a 4- to 7-membered sultam comprising the nitrogen atom and the $S(O)_2$ group that bear them;

$R_8$ represents a halogen atom or a group $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl, $C_1$-$C_6$-alkoxy, $C_3$-$C_7$-cycloalkyloxy, $C_3$-$C_7$-cycloalkyl-$C_1$-$C_3$-alkylenoxy, $C_1$-$C_6$-fluoroalkoxy, nitro, cyano, $NR_3R_4$, —C(O)—$C_1$-$C_6$-alkyl or —C(O)—$C_3$-$C_7$-cycloalkyl; the groups $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl, $C_1$-$C_6$-alkoxy, $C_3$-$C_7$-cycloalkyloxy and $C_3$-$C_7$-cycloalkyl-$C_1$-$C_3$-alkylenoxy possibly being substituted with a group OH, $C_1$-$C_6$-alkoxy or $NR_3R_4$;

the sulfur atom(s) of the compound of formula (I) optionally being in oxidized form; the nitrogen atom(s) of the compound of formula (I) optionally being in oxidized form; or an acid-addition salt thereof.

2. The compound of formula (I) according to claim 1, wherein:
$X_1$, $X_2$, $X_3$ and $X_4$ represent, independently of each other, a group C—$R_1$; and
$R_1$ is as defined in formula (I) according to claim 1;
or an acid-addition salt thereof.

3. The compound of formula (I) according to claim 1, wherein:
$X_1$, $X_2$ and $X_3$ represent a group C—$R_1$; $X_4$ represents a nitrogen atom; and
$R_1$ is as defined in formula (I) according to claim 1;
or an acid-addition salt thereof.

4. The compound of formula (I) according to claim 1, wherein $R_1$ is chosen from a hydrogen atom, a halogen atom and a group $C_1$-$C_6$-fluoroalkyl;
or an acid-addition salt thereof.

5. The compound of formula (I) according to claim 1, wherein n is equal to 1;
or an acid-addition salt thereof.

6. The compound of formula (I) according to claim 1, wherein Y represents an aryl optionally substituted with one or more halogen atoms;
or an acid-addition salt thereof.

7. The compound of formula (I) according to claim 1, wherein W represents an oxygen atom;
or an acid-addition salt thereof.

8. The compound of formula (I) according to claim 1, wherein:
A represents a bicyclic heteroaryl of formula:

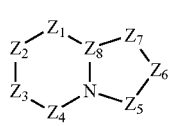

wherein:
$Z_1$, $Z_2$, $Z_3$ and $Z_4$ represent, independently of each other, a carbon atom or a nitrogen atom;
$Z_5$, $Z_6$ and $Z_7$ represent, independently of each other, a nitrogen atom or a group C—$R_{2b}$;
$Z_8$ represents a carbon atom;
wherein two, at most, from among $Z_1$, $Z_2$, $Z_3$, $Z_4$, $Z_5$, $Z_6$ and $Z_7$ represent a nitrogen atom;
one from among $Z_1$, $Z_2$, $Z_3$ and $Z_4$, corresponding to a carbon atom, being bonded to the nitrogen atom of the amide or thioamide of formula (I); and $R_{2b}$ represents a hydrogen atom or a group $C_1$-$C_6$-alkyl, C(O)O—$C_1$-$C_6$-alkyl, phenyl or thienyl; the groups $C_1$-$C_6$-alkyl optionally being substituted with a hydroxyl or $C_1$-$C_6$-alkoxy group;
or an acid-addition salt thereof.

9. The compound of formula (I) according to claim 1, wherein:
A represents the group:

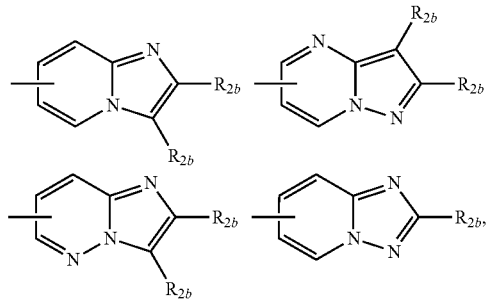

$R_{2b}$ represents a hydrogen atom or a group $C_1$-$C_6$-alkyl, C(O)O—$C_1$-$C_6$-alkyl, phenyl or thienyl; the groups $C_1$-$C_6$-alkyl possibly being substituted with a hydroxyl or $C_1$-$C_6$-alkoxy group;
or an acid-addition salt thereof.

10. The compound of formula (I) according to claim 1, wherein:
A represents the group:

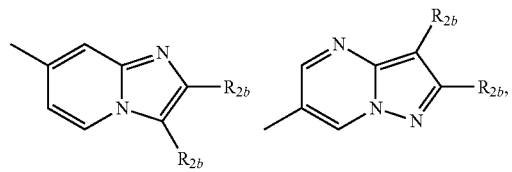

$R_{2b}$ represents a hydrogen atom or a group $C_1$-$C_6$-alkyl, phenyl or thienyl; the groups $C_1$-$C_6$-alkyl optionally being substituted with a hydroxyl or $C_1$-$C_6$-alkoxy group;
or an acid-addition salt thereof.

11. The compound of formula (I) according to claim 1, wherein:
$X_1$, $X_2$, $X_3$ and $X_4$ represent, independently of each other, a group C—$R_1$; or alternatively $X_1$, $X_2$ and $X_3$ represent a group C—$R_1$; $X_4$ represents a nitrogen atom;
$R_1$ is chosen from a hydrogen atom, a halogen atom or a group $C_1$-$C_6$-fluoroalkyl;
n is equal to 1;
Y represents an aryl optionally substituted with one or more halogen atoms;
W represents an oxygen atom;
A represents a bicyclic heteroaryl of formula:

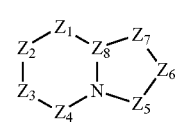

wherein:

$Z_1$, $Z_2$, $Z_3$ and $Z_4$ represent, independently of each other, a carbon atom or a nitrogen atom;

$Z_5$, $Z_6$ and $Z_7$ represent, independently of each other, a nitrogen atom or a group C—$R_{2b}$;

$Z_8$ represents a carbon atom;

wherein two, at most, from among $Z_1$, $Z_2$, $Z_3$, $Z_4$, $Z_5$, $Z_6$ and $Z_7$ represent a nitrogen atom;

one from among $Z_1$, $Z_2$, $Z_3$ and $Z_4$, corresponding to a carbon atom, being bonded to the nitrogen atom of the amide or thioamide of formula (I); and $R_{2b}$ represents a hydrogen atom or a group $C_1$-$C_6$-alkyl, C(O)O—$C_1$-$C_6$-alkyl, phenyl or thienyl; the groups $C_1$-$C_6$-alkyl optionally being substituted with a hydroxyl or $C_1$-$C_6$-alkoxy group;

or an acid-addition salt thereof.

12. The compound of formula (I) according to claim 1, chosen from:

N-(2,3-Dimethylimidazo[1,2-c]pyrid-7-yl)-5-fluoro-1-[(3-fluorophenyl)methyl]-1H-indole-2-carboxamide;

N-(2,3-Dimethylimidazo[1,2-a]pyrid-6-yl)-5-fluoro-1-[(3-fluorophenyl)methyl]-1H-indole-2-carboxamide;

N-[2-(Hydroxymethyl)imidazo[1,2-a]pyrid-6-yl]-5-fluoro-1-[(3-fluorophenyl)methyl]-1H-indole-2-carboxamide;

N-(3-Methyl-2-phenylimidazo[1,2-a]pyrid-6-yl)-5-fluoro-1-[(3-fluorophenyl)methyl]-1H-indole-2-carboxamide;

N-(2-Ethylimidazo[1,2-c]pyrid-6-yl)-5-fluoro-1-[(3-fluorophenyl)methyl-1H-indole-2-carboxamide;

N-[2-(Thien-2-yl)imidazo[1,2-a]pyrid-6-yl]-5-fluoro-1-[(3-fluorophenyl)methyl]-1H-indole-2-carboxamide;

N-(2-tert-Butylimidazo[1,2-a]pyrid-6-yl)-5-fluoro-1-[(3-fluorophenyl)methyl]-1H-indole-2-carboxamide;

N-[2-Methoxymethylimidazo[1,2-a]pyrid-7-yl)-5-fluoro-1-[(3-fluorophenyl)methyl]-1H-indole-2-carboxamide;

N-[2-(Hydroxymethyl)imidazo[1,2-a]pyrid-7-yl]-5-fluoro-1-[(3-fluorophenyl)methyl]-1H-indole-2-carboxamide;

N-(2-Methyl-3-phenylimidazo[1,2-a]pyrid-7-yl)-5-fluoro-1-[(3-fluorophenyl)methyl]-1H-indole-2-carboxamide;

N-[2-(Thien-2-ylimidazo[1,2-c]pyrid-7-yl)-5-fluoro-1-[(3-fluorophenyl)methyl]-1H-indole-2-carboxamide;

N-(2-Ethylimidazo[1,2-a]pyrid-7-yl)-5-fluoro-1-[(3-fluorophenyl)methyl-1H-indole-2-carboxamide;

N-(2-tert-Butylimidazo[1,2-a]pyrid-7-yl)-5-fluoro-1-[(3-fluorophenyl)methyl]-1H-indole-2-carboxamide;

N-(2,3-Dimethylimidazo[1,2-a]pyrid-7-yl)-5-trifluoromethyl-1-[(3-fluorophenyl)methyl]-1H-indole-2-carboxamide;

N-(2-Ethylimidazo[1,2-a]pyrid-7-yl)-5-trifluoromethyl-1-[(3-fluorophenyl)methyl]-1H-pyrrolo[2,3-b]pyridine-2-carboxamide;

N-(2,3-Dimethylimidazo[1,2-a]pyrid-7-yl)-5-trifluoromethyl-1-[(3-fluorophenyl)methyl]-1H-pyrrolo[2,3-b]pyridine-2-carboxamide;

N-[2-(Hydroxymethyl)imidazo[1,2-a]pyrid-7-yl]-5-trifluoromethyl-1-[(3-fluorophenyl)methyl]-1H-indole-2-carboxamide;

N-[2-(Hydroxymethyl)imidazo[1,2-a]pyrid-7-yl]-5-trifluoromethyl-1-[(3-fluorophenyl)methyl]-1H-pyrrolo[2,3-b]pyridine-2-carboxamide;

N-(2-Methylimidazo[1,2-a]pyrid-7-yl)-5-fluoro-1-[(3-fluorophenyl)methyl]-1H-indole-2-carboxamide;

N-(2-Methylpyrazolo[1,5-a]pyrimidin-6-yl)-5-fluoro-1-[(3-fluorophenyl)methyl]-1H-indole-2-carboxamide;

N-[2-(Ethyloxycarbonyl)imidazo[1,2-b]pyridazin-6-yl]-5-fluoro-1-[(3-fluorophenyl)methyl]-1H-indole-2-carboxamide;

N-[(2-(Ethyloxycarbonyl)imidazo[1,2-a]pyrid-6-yl)-5-fluoro-1-[(3-fluorophenyl)methyl]-1H-indole-2-carboxamide;

N-(2-Methylimidazo[1,2-a]pyrid-6-yl)-5-fluoro-1-[(3-fluorophenyl)methyl]-1H-indole-2-carboxamide; and N-([1,2,4]Triazolo[1,5-a]pyrid-6-yl)-5-fluoro-1-[(3-fluorophenyl)methyl]-1H-indole-2-carboxamide;

or an acid-addition salt thereof, or a hydrate or solvate thereof.

13. A process for preparing a compound of formula (I) according to claim 1, comprising reacting a compound of formula (II):

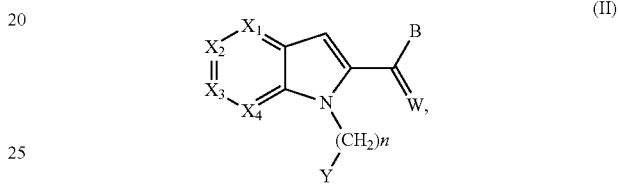

in which $X_1$, $X_2$, $X_3$, $X_4$, n, Y and W are as defined in formula (I) according to claim 1, with a compound of formula (III):

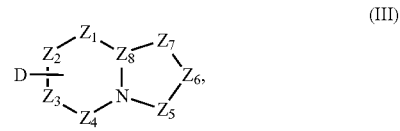

in which $Z_1$, $Z_2$, $Z_3$, $Z_4$, $Z_5$, $Z_6$, $Z_7$ and $Z_8$ are as defined in formula (I) according to claim 1: and when B represents an $NH_2$ group and D represents a leaving group, either in the presence of a copper salt in catalytic amount, a copper ligand in catalytic amount and a base, in a solvent; or in the presence of a catalytic amount of a palladium derivative, a catalytic amount of a palladium ligand and a base, in a refluxing solvent;

when B represents a hydroxyl group and D represents an $NH_2$ group, in the presence of a coupling agent in a solvent; or when B is a chlorine atom and D represents an $NH_2$ group, in a solvent.

14. A process for preparing a compound of formula (I) according to claim 1, in which W represents an oxygen atom and A represents a group:

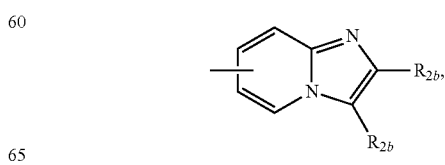

comprising reacting a compound of formula (V):

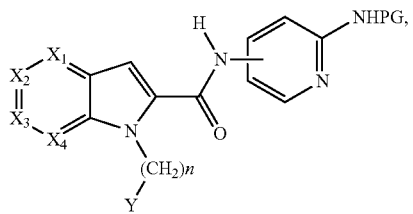
(V)

in which $X_1$, $X_2$, $X_3$, $X_4$, n and Y are as defined in formula (I) according to claim 1 and PG represents a hydrogen atom,
with a compound of formula (IV):

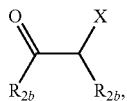
(IV)

in which X represents a leaving group and $R_{2b}$ is as defined in formula (I) according to claim 1.

15. A pharmaceutical composition comprising a compound of formula (I) according to claim 1, or a pharmaceutically acceptable acid addition salt thereof, in combination with at least one pharmaceutically acceptable excipient.

16. A pharmaceutical composition comprising a compound of formula (I) according to claim 9, or a pharmaceutically acceptable acid addition salt thereof, in combination with at least one pharmaceutically acceptable excipient.

17. A pharmaceutical composition comprising a compound of formula (I) according to claim 12, or a pharmaceutically acceptable acid addition salt thereof, in combination with at least one pharmaceutically acceptable excipient.

* * * * *